United States Patent [19]

McCombie

[11] Patent Number: 5,064,837

[45] Date of Patent: Nov. 12, 1991

[54] 3-SUBSTITUTED-1-ARYL-2(H)-QUINOLONES AND THEIR PHARMACEUTICAL COMPOSITIONS

[75] Inventor: Stuart W. McCombie, Caldwell, N.J.

[73] Assignee: Schering Corporation, Kenilworth, N.J.

[21] Appl. No.: 435,148

[22] Filed: Nov. 13, 1989

[51] Int. Cl.$^5$ .................. A61K 31/47; C07D 215/227
[52] U.S. Cl. .................................... 514/312; 544/182; 544/238; 544/333; 544/405; 546/157
[58] Field of Search .......................... 546/157; 514/312

[56] References Cited

U.S. PATENT DOCUMENTS

| 4,277,479 | 7/1981 | Nishi et al. | 546/157 |
| 4,735,948 | 4/1988 | Wright | 514/299 |
| 4,748,246 | 5/1988 | Skotnicki et al. | 544/331 |

FOREIGN PATENT DOCUMENTS

| 0120483 | 10/1984 | European Pat. Off. |
| 0226357 | 6/1987 | European Pat. Off. |
| 0236140 | 9/1987 | European Pat. Off. |
| 54-073783 | 6/1979 | Japan | 546/157 |
| 988776 | 4/1965 | United Kingdom |

OTHER PUBLICATIONS

Chemical Abstract 211280h, vol. 91, No. 26 (24 Dec. 79) and Reg. No. 71978-18-2 (13 Jun. 79); and Derwent Abstract 55102b.
Chemical Abstract 221701e, vol. 108, No. 25 (20 Jun. 88), and Reg. No. 114560-96-2 and Reg. No. 114560-71-3 (21 Oct. 87).
Chemical Abstract 204453h, vol. 18, No. 14, (4 Apr. 88), and Reg. NO. 114125-87-0.
Chupp and Metz, Heterocycles from Substituted Amides, VI (1,2). J. heterocyclic Chem., 16. pp. 65–71, 1979.
Chemical Abstract 92023s, vol. 79, 1973.
Hayes, et al., J. Chem. Research(s) 414, (1980).
Meth–Cohn et al., J.C.S. Perkin I 1520 (1981).

Primary Examiner—Bernard Dentz
Attorney, Agent, or Firm—Gerald S. Rosen; Henry C. Jeanette

[57] ABSTRACT

Novel 3-substituted-1-aryl-2(1H)-quinolones useful as anti-allery, anti-inflammatory, anti-hyperproliferative skin disease agents are disclosed. The quinolones are represented by Formula 1:

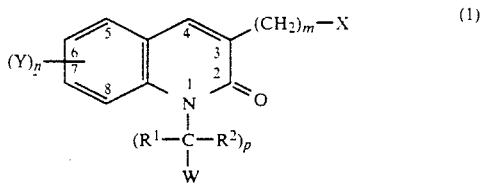

Pharmaceutical compositions and methods of treatment employing such compounds are also disclosed.

17 Claims, No Drawings

3-SUBSTITUTED-1-ARYL-2(H)-QUINOLONES AND THEIR PHARMACEUTICAL COMPOSITIONS

FIELD OF THE INVENTION

This invention relates to novel 3-substituted-1-aryl-2(1H)-quinolones which are useful as anti-allergy and anti-inflammatory agents.

BACKGROUND OF THE INVENTION

U.S. Pat. No. 4,748,246 discloses substituted pyrazolo [4.3-C] quinolines having the formula:

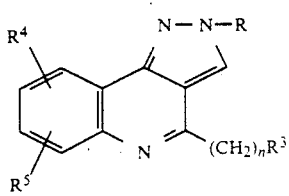

which are disclosed as being able to antagonize the activity of interleukin-1 (IL-1) and as being useful as anti-inflammatory agents in the treatment of disease states involving enzymatic tissue destruction.

European Patent Application, Publication No. 0 120 483A1 published Oct. 3, 1984 (Application No. 84103231.1 filed Mar. 23, 1984) discloses (1H-tetrazol-5-yl)-2(1H)-quinolones of the formula:

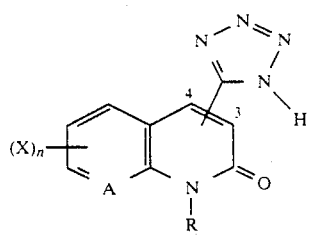

In the formula "A" is —CH= or —N=; "R" is H or alkyl of 1-4C; "n" is 0, 1 or 2; and "X" is H, alkyl of 1-4C, alkoxy of 1-4C, halogen, methylmercapto, methylsulfonyl, or two X's can be combined as methylenedioxy; with the proviso that, when X is methylmercapto or methylsulfonyl, then n must be 1. The document discloses that the compounds are useful as anti-allergy agents.

European Patent Application, Publication No. 0 226 357A1, published June 24, 1987 (Application No. 86309207.8 filed Nov. 11, 1986) discloses substituted 2-(1H)-quinolones of the formula:

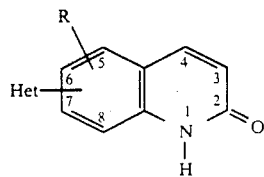

In the formula "Het" is a 5-membered monocyclic aromatic heterocyclic group containing at least one nitrogen atom in the aromatic ring and attached by a nitrogen atom to the 5-, 6-, 7- or 8- position of the quinolone. In the formula "R", which is attached to the 5-, 6-, 7- or 8-position of the quinolone, is H, $C_1$–$C_4$ alkyl, $C_1$–$C_4$ alkoxy, hydroxy, $CF_3$, halo, cyano or hydroxymethyl. According to the document, these compounds are cardiac stimulants.

Commonly used non-steroidal anti-inflammatory agents such as aspirin, indomethacin and piroxicam act by inhibiting the cyclooxygenase enzyme, frequently leading to such side effects as gastric irritation and ulcers. Thus, there is a need for compounds with anti-inflammatory properties which do not cause or show a marked reduction in the incidence of such side effects. This invention provides compounds having anti-inflammatory as well as anti-allergy activity which affects both 5-lipoxygenase (5-LO) and cyclooxygenase (CO) derived mediators and should lead to less incidence of serious side effects.

SUMMARY OF THE INVENTION

The compounds of this invention have particularly advantageous properties useful in the treatment of inflammatory and allergic reactions. Without wishing to be bound by theory, it is believed that the compounds of this invention do not directly inhibit the CO or the 5-LO enzyme and thus do not cause side effects which result from such inhibition. In addition, the compounds of this invention cause a reduction in the formation of interleukin-1 (IL-1) which is known to be involved in serious inflammatory diseases such as arthritis.

The compounds of this invention are represented by Formula I:

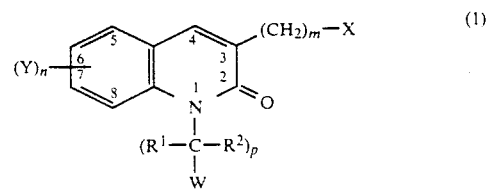

or a pharmaceutically acceptable salt or solvate thereof, wherein:

$R^1$ and $R^2$ are the same or different and each is independently selected from H and alkyl;

p is an integer from 0 to 2;

Y is in the 5-, 6-, 7-, and/or 8-position of the quinolone ring and Y is selected from:
(1) halo;
(2) —$NO_2$;
(3) —CN;
(4) alkyl;
(5) alkyl substituted with one or more halo atoms independently selected from F, Cl, Br, and I;
(6) alkenyl;
(7) alkynyl;
(8) cycloakyl;
(9) cycloalkenyl;
(10) acyl;
(11) carboxyl;
(12) heterocyclyl;
(13) aryl;
(14) aralkyl;
(15) alkaryl;
(16) heteroaryl;
(17) aroyl;
(18) heteroaroyl;
(19) —$QR^3$ wherein $R^3$ is selected from alkyl, acyl, aryl, heteroaryl, aroyl, and heteroaroyl and wherein Q is selected from S, O, and —NR$^4$, wherein R$^4$ is selected from:
(a) H;
(b) alkyl;
(c) acyl;
(d) cycloalkyl;
(e) heterocyclyl;
(f) aryl;
(g) alkaryl;
(h) aralkyl;
(i) aroyl
(j) heteroaryl; and
(k) heteroaroyl;
(20) —OR$^5$, wherein R$^5$ is selected from H, cycloalkyl, heterocyclyl, alkaryl, and aralkyl;
(21) —CO$_2$R$^{4'}$; wherein R$^{4'}$ is selected from
(a) H;
(b) alkyl;
(c) cycloalkyl;
(d) heterocyclyl;
(e) aryl;
(f) alkaryl;
(g) aralkyl; and
(h) heteroaryl
(22) —N(R$^4$)$_2$ wherein each R$^4$ is the same or different and is as defined above;
(23) —S(O)$_q$R$^{4'}$ wherein q is an integer 1 to 2; and R$^{4'}$ is as defined above;
(24) —SR$^4$ wherein R$^4$ is as defined above;
(25) —Q$_r$C(O)R$^6$Z(R$^{4'}$)$_t$, wherein r is an integer from 0 to 1, Z is selected from N, S, or O, R$^6$ is an alkylene group having from 1 to 6 carbon atoms, t is 1 when Z is S or O, and when Z is N then t is 2 and each R$^{4'}$ is the same or different and is as defined above;
(26) —NHC(O)R$^4$ and R$^4$ is as defined above;
(27) —NHSO$_2$R$^{4'}$ and R$^{4'}$ is as defined above; and
(28) —SO$_2$N(R$^7$)2; wherein each R$^7$ is the same or different and R$^7$ is independently selected from H, alkyl and aryl;
n is an integer from 0 to 2 and when n is 2 each Y is the same or different;
X is selected from:
(1) —S(O)$_q$R$^{4'}$;
(2) —SR$^4$;
(3) —N(R$^4$)2 wherein each R$^4$ is the same or different;
(4) —N$_3$;
(5) —NHC(O)R$^4$;
(6) —Q$_r$C(O)R$^6$Z(R$^{4'}$)$_t$;
(7) —Q$_r$C(O)R$^6$OH;
(8) —QR$^3$;
(9) heteroaryl;
(10) heteroaroyl;
(11) heterocyclyl, wherein said heterocyclyl is bound through a carbon atom, or a nitrogen atom except when there is an oxygen or sulfur heteroatom also in the heterocyclyl ring;
wherein said q, R$^4$, R$^{4'}$, Q, r, R$^6$, Z and t, are as defined above for Y;
m is an integer from 0 to 2;
W is selected from aryl and heteroaryl, and W can optionally be substituted with up to three groups wherein each group is the same or different and is independently selected from:
(1) —OH;
(2) hydroxymethyl;
(3) alkyl;
(4) halo;
(5) —NO$_2$;
(6) alkoxy;
(7) —CF$_3$;
(8) —CN;
(9) cycloalkyl;
(10) alkynyloxy;
(11) alkenyloxy;
(12) S(O)$_q$R$^{4'}$;
(13) —SR$^4$;
(14) —C(O)R$^8$, wherein R$^8$ is selected from —OH, —N(R$^4$)$_2$, and —OR$^9$, and R$^9$ is alkyl;
(15) —O—(CH$_2$)$_v$—C(O)R$^8$ wherein v is an integer from 1 to 4 R$^8$ is as defined above;
(16) —N(R$^4$)$_2$; and
(17) —NHC(O)H;
wherein q, R$^{4'}$ and R$^4$ are as defined above for Y;
with the proviso that in Formula 1 when R$^3$ and R$^4$ are heteroatom containing groups, said heteroatom containing groups, when bound to a S, N, or O atom, is bound through a carbon atom of the heteroatom containing group;
with the proviso that in Formula 1 when p is 0 and W is a heteroatom containing group, then W is bound through a carbon atom in the W group; and
wherein in formula 1, alkyl, alkenyl, alkynyl, cycloalkyl, cycloalkenyl, acyl, carboxyl, heterocyclyl, aryl, aralkyl, alkaryl, heteroaryl, aroyl and heteroaroyl are as defined hereinafter.

In preferred compounds of formula (1), Y is selected from:
(1) halo, wherein said halo is selected from F, Br, and Cl;
(2) —C(H)$_{3-b}$G$_b$ wherein b is an integer from 1 to 3 and G is a halo atom selected from F, Br and Cl;
(3) —OR$^{10}$, wherein R$^{10}$ is selected from H, alkyl, aryl, and heteroaryl;
(4) —O—C(O)R$^4$;
(5) —NO$_2$;
(6) —NH$_2$;
(7) —NHR$^{11}$ wherein R$^{11}$ is selected from alkyl, aryl, and heteroaryl;
(8) —NHC(O)R$^4$;
(9) —NHSO$_2$R$^{4'}$;
(10) —NHSR$^4$;
(11) —NR$^{12}$R$^{13}$ wherein R$^{12}$ is selected from alkyl and aryl, and R$^{13}$ is —C(O)R$^4$;
(12) —S(O)$_q$R$^{12}$ wherein R$^{12}$ is as above defined;
(13) —SH;
(14) —SO$_2$N(R$^{10}$)$_2$ wherein each R$^{10}$ is the same or different and R$^{10}$ is as defined in (3) above;
wherein
R$^4$, R$^{4'}$ and q are as above defined for Y;
X is selected from:
(1) —S(O)$_q$R$^{4'}$;
(2) —SR$^4$;
(3) —N(R$^4$)$_2$;
(4) —N$_3$;
(5) —NHC(O)R$^4$;
(6) —NR$^4$R$^{14}$ wherein R$^{14}$ is selected from acyl, aryl, aroyl, heteroaroyl, and heteroaryl;
(7) -S-heteroaryl;
(8) heteroaryl; and
(9) heteroaroyl;
wherein
q, R$^4$ and R$^{4'}$, are as defined above for Y; and
W is selected from pyrazinyl, pyridazinyl, pyridyl, pyrimidyl and phenyl and is bound through a carbon atom when p is zero. In this preferred embodiment all variables not specifically mentioned are the same as defined above for formula (1).

In more preferred compounds of formula (1), X is selected from: —SR[4]; —S(O)$_q$R[4']; imidazolyl; indolyl; oxazolyl; oxadiazolyl; pyrazinyl; pyrazolyl; pyridazinyl; pyridyl; pyrimidyl; pyrrolyl; thiadiazolyl; thiazolyl; triazinyl; triazolyl; tetrazolyl; —N$_3$; and —NHC(O)R[4]. The substituent X may also be benzothiofuranyl, and when X is benzothiofuranyl or indolyl these substituents are bound through their benzenoid ring or through nitrogen or carbon on their hetero ring. In these compounds, when p is zero, W is bound through a carbon atom and when X, Y or W is a heterocyclic with an O or S heteroatom, it is bound through a carbon atom. All variables of formula (1) except those mentioned herein are as defined for formula (1).

The most preferred compounds of formula (1) are wherein p is 0, W is phenyl, and X is selected from: —SCH$_3$, —S(O)CH$_3$, 1-triazolyl, and 1-tetrazolyl and the remaining variables are as defined for formula (1).

In the compounds of this invention, m is preferably 1 or 2 and most preferably m is 1.

Preferred compounds of this invention are represented by Formulas 2-6:

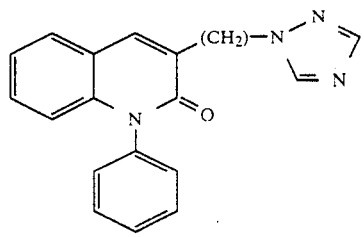
(2)

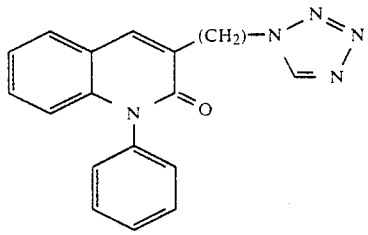
(3)

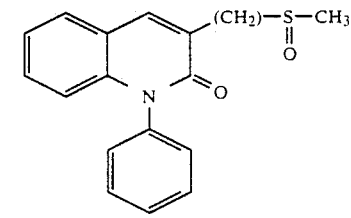
(4)

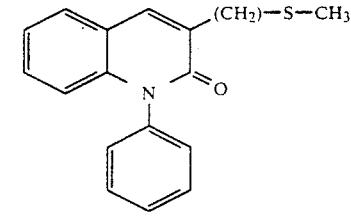
(5)

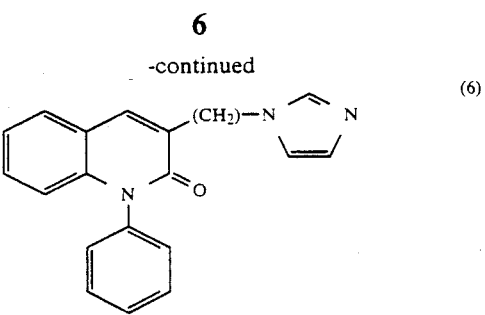
(6)

Of the preferred compounds the most preferred compound is that of Formula (2).

This invention also provides pharmaceutical compositions, useful for treating inflammation, allergy, and/or hyperproliferative skin disease (such as psoriasis), comprising an effective amount of a compound represented by Formula (1) in combination with a pharmaceutically acceptable carrier preferably oral compositions for treating allergy and inflammation and topical compositions for treating hyperproliferative skin diseases. Preferably the compounds utilized are those represented by Formulas 2-6, with Formula (2) being most preferred.

This invention further provides a method for treating allergy in a subject in need of such treatment, comprising administering to said subject an anti-allergy effective amount of a compound represented by Formula (1). Preferably compounds represented by Formulas 2-6 are used with Formula (2) being most preferred and the administration is preferably oral.

This invention additionally provides a method of treating inflammation in a subject in need of such treatment, by administering, preferably orally, to said subject an anti-inflammatory effective amount of a compound represented by Formula (1), preferably Formulas 2 to 6, and most preferably Formula (2).

This invention still further provides a method of treating hyperproliferative skin disease in a subject in need of such treatment, comprising administering, preferably topically, although oral administration can be effective, to said subject an anti-hyperproliferative effective amount of a compound represented by Formula (1), preferably Formulas 2-6, and most preferably Formula (2).

DETAILED DESCRIPTION OF THE INVENTION

When used herein, the terms listed below have the following scope, unless indicated otherwise.

acyl—represents -C(O)-alkyl, -C(O)-alkenyl, -C(O)-alkynyl, -C(O)-cycloalkyl, -C(O)-cycloalkenyl or -C(O)-cycloalkynyl;

alkaryl—represents an aryl group, as defined below, in which an alkyl group, as defined below, is substituted for one of the aryl H atoms;

alkenyl—represents straight and branched carbon chains having at least one carbon to carbon double bond and preferably having from 2 to 6 carbon atoms;

alkenyloxy—represents straight and branched carbon chains having at least one carbon to carbon double bond and, unless otherwise specified, contains from 3 to 6 carbon atoms, the alkenyl thereof being bonded to an adjacent structural element through an oxygen atom;

alkoxy—represents an alkyl radical attached to a molecule through an oxygen atom (-O-alkyl);

alkyl—represents straight or branched carbon chains, which contain from 1 to 6 carbon atoms unless otherwise specified;

alkylamino—represents an —$NH_2$ group in which one or more of the hydrogens is substituted with an alkyl group as defined above;

alkynyl—represents straight and branched carbon chains having at least one carbon to carbon triple bond and preferably having from 2 to 6 carbon;

alkynyloxy—represents straight and branched carbon chains having at least one carbon to carbon triple bond and, unless otherwise specified, contains from 3 to 6 carbon atoms, the alkynyl group thereof being bonded to an adjacent structural element through an oxygen;

aralkyl—represents an alkyl group, as defined above, in which an aryl group as defined below is substituted for one of the alkyl H atoms;

aroyl—represents -C(O)-aryl wherein aryl is as defined below;

aryl—represents a carbocyclic group containing from 6 to 15 carbon atoms and having at least one aromatic ring (e.g., a phenyl or fused ring), with all available substitutable carbon atoms of the carbocyclic group being intended as possible points of attachment, said carbocyclic group being optionally substituted with 1 to 3 groups, each independently selected from halo, alkyl, hydroxy, alkoxy, phenoxy, amino, alkylamino, dialkylamino.

carboxyl—represents a —C(O)OH group;

cycloalkenyl—represents a carbocyclic ring having from 3 to 7 carbon atoms and at least one carbon to carbon double bond in the ring;

cycloalkyl—represents a saturated carbocyclic ring having from 3 to 7 carbon atoms;

halo-represents fluoro, chloro, bromo or iodo with fluoro, chloro and bromo being preferred;

heteroaryl (including the heteroaryl portion of heteroarylmethyl)-represents cyclic groups having at least one O, S and/or N heteroatom interrupting a carbocyclic ring structure and having a sufficient number of delocalized pi electrons to provide aromatic character, with the aromatic heterocyclic groups preferably containing from 3 to 14 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-,, 4-, 5-, 6- or 7-benzofuranyl, 2-, 3-, 4-, 5-, 6- or 7-indolyl, 3-, 4- or 5-pyrazolyl, 2-, 4- or 5-oxazolyl, and the like. Preferred heteroaryl groups are pyridyl, 2- or 3-furyl, 3-thienyl, 2-, 4- or 5-imidazolyl, 7-indolyl; 1-triazolyl, 4-triazolyl, 1 or 2-tetrazolyl;

heteroaroyl—represents -C(O)-heteroaryl, wherein heteroaryl is as defined above;

heterocyclyl—represents a non-aromatic ring containing from 3 to 7 carbon atoms, which may optionally contain at least one carbon-to-carbon double or triple bond, and which contains at least one heteroatom selected from nitrogen, oxygen or sulfur; representative examples of heterocycles include, but are not limited to: pyrrolidone, piperidine, piperazine, heptamethyleneimine, hexamethyleneimine, homopiperazine, perhydroindole, azetidine, 4-piperidinopiperidine, 1-azacycloheptane, perhydroisoquinoline, decahydroquinoline, 1-phenylpiperazine, 4-phenylpiperidine, 1-(4-fluorophenyl)piperazine, 1,3,5-hexahydrotriazine, glycoluril (acetyleneurea), morpholine, phenylmorpholine, thiomorpholine, propylene sulfide, tetrahydrothiophene, thiazolidine, ω-thiocaprolactam, 1,4-thioxane, 1,3-dithiane, 1,4,7-trithiacyclononane, 1,3,5-trithiane, pentamethylene sulfide, 1,5-dithiacyclooctan-3-ol, 1,4-dithiaspiro [4.5]decan-8-ol, ethylene sulfide, tetrahydrofuran, tetrahydropyran, 2,4,8,10-tetraoxaspiro[5.5]undecane, trimethylene oxide, 1,3,5-trioxane, oxepane, and the like.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum, salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

The compounds of Formula (1) can be prepared by the processes described below. In these processes the substituents are as described above, unless indicated otherwise. Those skilled in the art will appreciate that in the processes described below the reactions are carried out at a temperature which allows the reaction to proceed at a reasonable rate, but not so high as to cause undue degradation of reactants and/or products.

In addition, protecting groups are needed when reactions are to be performed on compounds in which the aromatic ring, either in the quinolone or attached to the nitrogen, is to be substituted with —OH, —$NH_2$ or —NHR. Such protecting groups are removable by conventional means.

Suitable phenolic hydroxy protecting groups are benzyl, methyl, triisopropylsilyl, benzoyl, and acetyl.

Suitable amino protecting groups are methoxycarbonyl, benzyloxycarbonyl, phthaloyl, and t-butoxycarbonyl.

Equation (abbreviated "EQ") I, represents a preferred method for preparing the compounds represented by Formula (1) and preferably those of Formula (2):

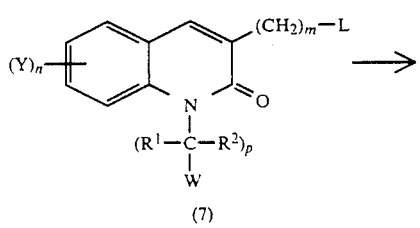

(7)

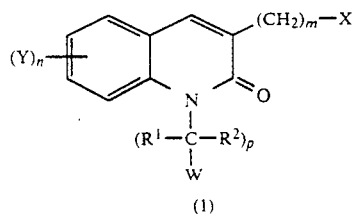

(1)

In EQ I, the compounds represented by Formula 7 are reacted with a nucleophile, XH or X- (from M+X- wherein M+ is an alkali metal such as sodium or potassium) to form the compounds represented by Formula 1. The reaction is usually carried out in the presence of a polar solvent such as dimethylformamide (DMF), dimethylsulfoxide (DMSO), tetrahydrofuran (THF), ethanol, methanol, and the like. Generally the reaction is conducted at a temperature within the range of about 25° C. to about 100° C. with about 25° C. to about 50° C. being preferred. In EQ I m can be 1 or 2, but can not be zero. The leaving group, L, is usually Cl, but may be Br, I, $OSO_2CH_3$, and the like. The nucleophile (XH or X−) is used as the free base or in the anionic form depending on the reaction conditions utilized, or the reaction run. For example, the free base may be used when imidazole or an amine is the reactant, whereas the anionic form may be used when triazole, tetrazole or RSH is the reactant.

Representative examples of the free base form (XH) include basic amines such as $NH_3$, $R^aNH_2$ (wherein $R^a$ is alkyl, aryl, heterocyclyl), imidazole, and the like. Other nucleophiles should be used in the anionic form (X−) in the form of the salt of an alkali metal, such as sodium and potassium. Examples of the anionic form include but are not limited to: $Na^+[triazole]^-$, $Na^+N_3^-$, $Na^+S-R^a$, $Na^+[tetrazole]^-$, and the like.

Reactions according to EQ I carried out using unsymmetrical nucleophiles may give rise to isomeric mixtures, which are separated by techniques well known in the art —e.g., by chromatography, crystallization, and the like. For example, see EQ II-V below.

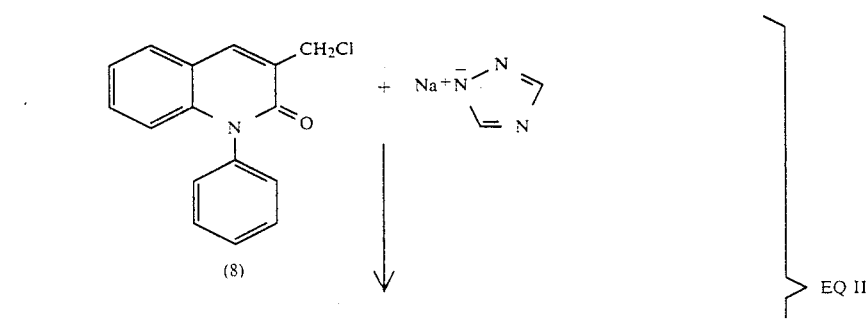

EQ II

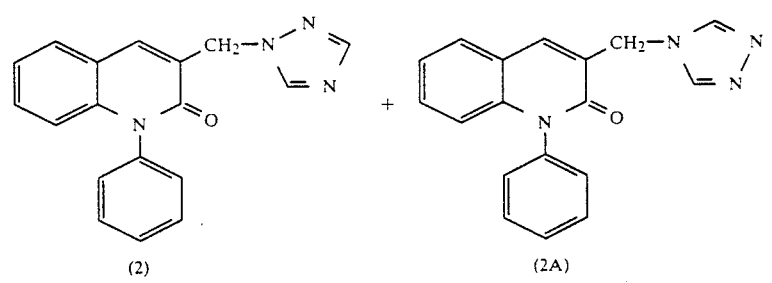

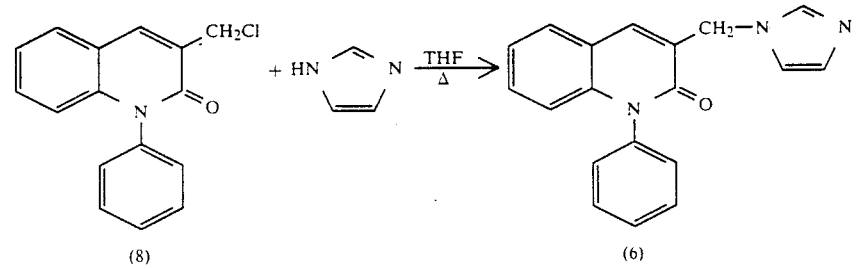

EQ III

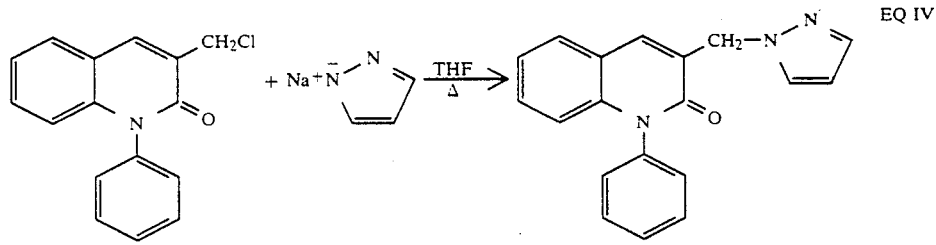

EQ IV

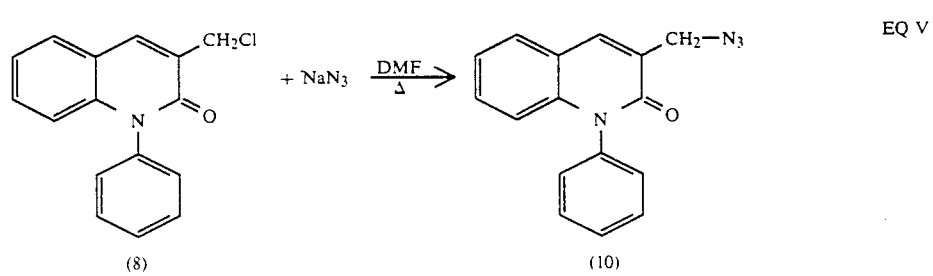

EQ V

EQ VI represents another method for preparing the compounds represented by Formula 1.

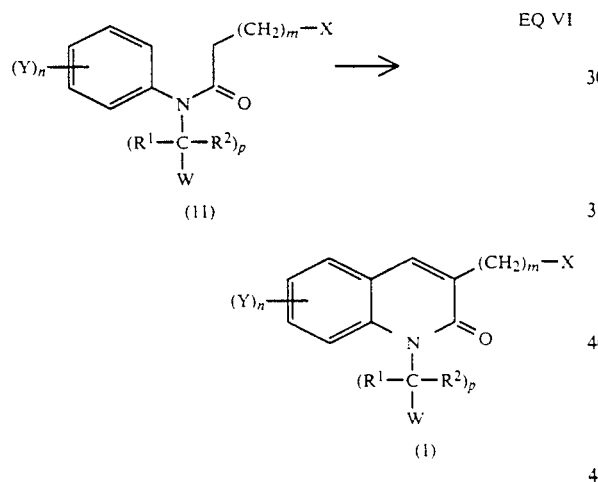

EQ VI

Generally, the reaction represented by EQ VI is carried out at a temperature within the range of about 50° C. to about 120° C. in the presence of a non-polar solvent such as 1,2-dichloroethane, DMF, and an activating agent such as $POCl_3$, $(COCl)_2$, and the like. For example, a compound represented by Formula (11) is heated at about 100° C. in the presence of $POCl_3$ and DMF to effect ring closure. Following heating water is added to complete the reaction by hydrolysis of the intermediate salt.

In EQ VI, m may be 0, 1 or 2. A few examples of these cyclizations are known in the literature, see for example Chupp., J. P., and Metz, S., J. Heterocyclic Chem, 1979, pages 65-71 and Meth-Cohn, et al., J. Chem. Soc., Perkin I, (1981) 1520-1530.

Also, in EQ VI, when p is zero and W is an aryl substituent, cyclization to give a compound of Formula (1) will take place in the desired manner when $(Y)_n$ represents one or more electron-donating groups such as $-OCH_3$, $-NHC(O)R^4$, and the like. When $(Y)_n$ is one or more electron-withdrawing groups such as $-SO_2N(R^7)_2$, -CN, and the like, this method is not satisfactory.

EQ VII represents another method for preparing the compounds represented by Formula (1).

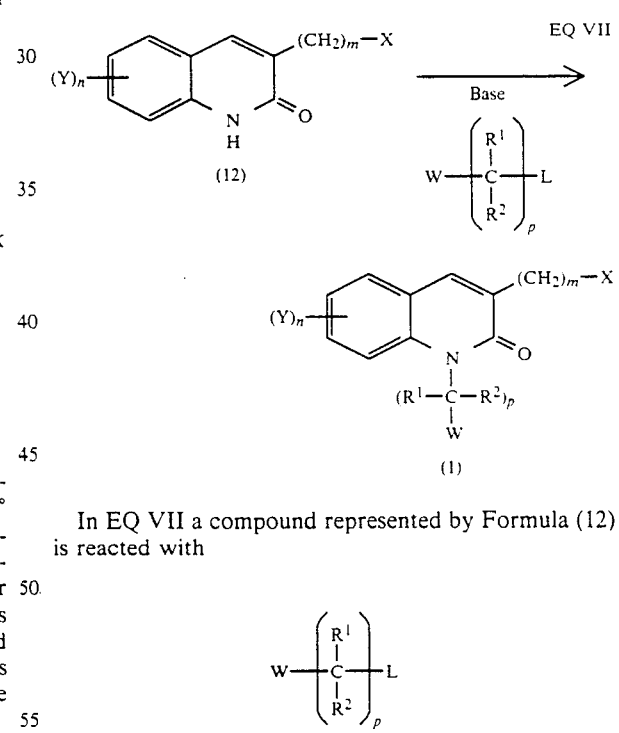

In EQ VII a compound represented by Formula (12) is reacted with

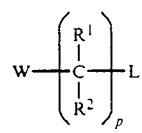

in the presence of a base to form compounds represented by structural Formula (1). Generally, the reaction is carried out a temperature within the range of about 25° C. to about 150° C. with about 25° C. to about 100° C. being preferred and about 25° C. being most preferred. In EQ VII m can be 0, 1, or 2, but p cannot be zero. L is a leaving group such as Cl, Br, I, $OSO_2CH_3$, $OSO_2C_6H_5$, and the like. The base can be any alkali hydride, such as NaH and the like, as well as any alkalialkoxide group, such as $NaO\ C_2H_5$ (sodium ethoxide), $KOt-C_4H_9$ (potassium tertiary butoxide), and the like.

Reactions represented by EQ VII, i.e., N-alkylation of 2-quinolones are well known in the art, for example see Deady et al., Aust. J. Chem., 30, 1349-52 (1977); for a general discussion see Boulton et al., eds. "Comprehensive Heterocyclic Chemistry" Vol. 2 pages 349-352 (1984) Pergamon Press.

example, European Patent Application, Publication Number 0 231 709.

EQ IX represents an alternative method to that presented in EQ VIII by using the ester (Formula 14, EQ IX) rather than the aldehyde (Formula 13, EQ VIII) to prepare compounds represented by Formula 1.

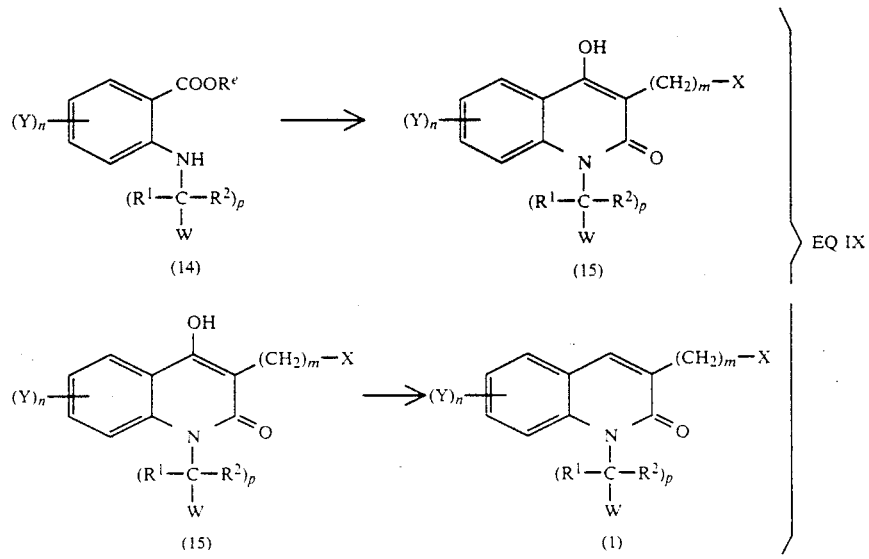

EQ VIII represents another method for preparing the compounds represented by Formula (1).

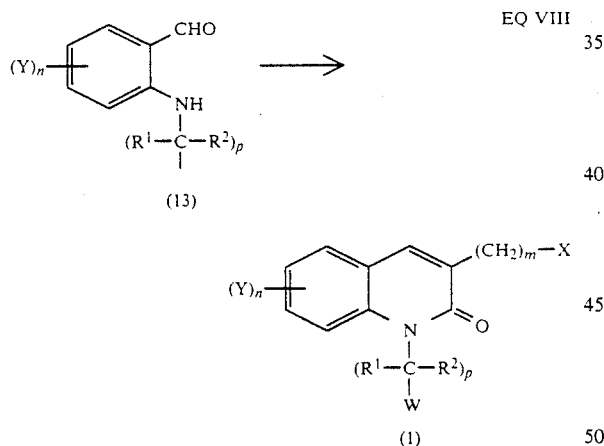

In EQ VIII, a compound represented by Formula (13) is heated with $(X(CH_2)_mCH_2CO)_2O$ and a base or is heated with $X(CH_2)_mCH_2COOR^b$ ($R^b$ is selected from 1-4 C alkyl) and a base to form the compounds represented by Formula (1). In EQ VIII m is 0, 1, or 2. Generally, the temperature utilized is within the range of about 25° C. to about 200° C. with about 50° C. to about 150° C. being preferred, and with about 100° C. being most preferred.

When the anhydride, $(X(CH_2)_mCH_2O)_2O$, is used in EQ VIII the base may be $NaHCO_3$ or the sodium salt of the carboxylic acid used for the anhydride. When the ester, $X(CH_2)_mCH_2OOR^b$, is used the base may be an alkali-alkoxide such as $NaOR^d$, $KOR^d$ and the like. $R^d$ may be the same as or different than $R^b$ and may be a lower alkyl group having 1 to 4 carbons. Examples include $NaOC_2H_5$, $KOt-C_4H_9$, and the like. See for In EQ IX, the compound represented by Formula 14 is reacted with the anhydride $(X(CH_2)_mCH_2O)_2$ or the ester $X(CH_2)_mCH_2COOR^b$ under the same conditions as the reaction presented in EQ VIII; however, in EQ IX the compound represented by structural Formula 15 compound is then deoxygenated by techniques known in the art see, Subrananion, et al., Synthesis, 481-485 (1984) to produce a compound represented by Formula 1. $R^b$ may be selected from 1-4 C alkyl.

EQ X-XB presents a method for preparing intermediates wherein m is 1 or 2.

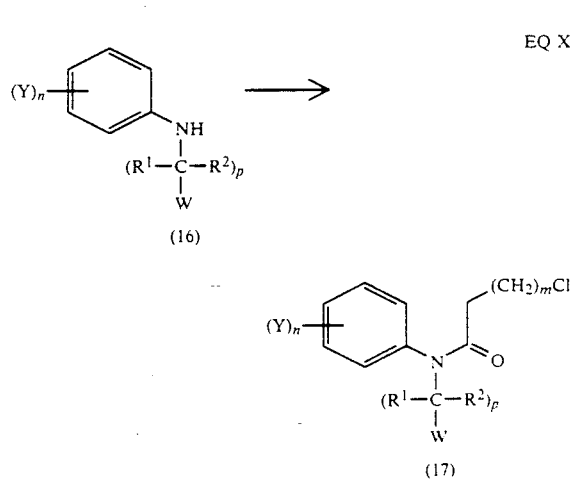

-continued

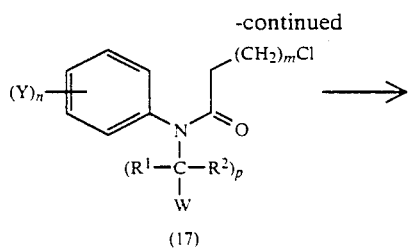
(17)

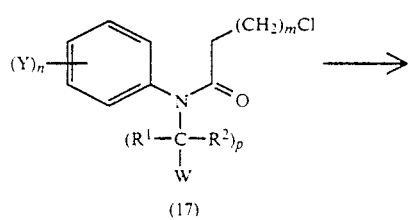
(11)

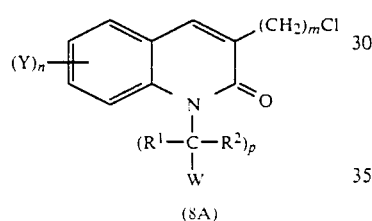
(17)

EQ X(A)

EQ X(B)

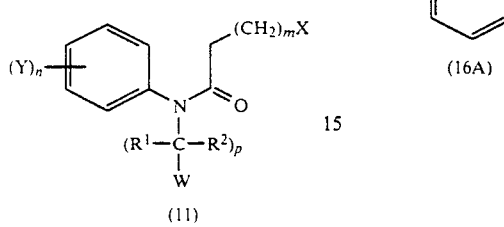
(8A)

In EQ X the N-substituted aniline derivative (Formula 16) is acylated by methods known in the art, e.g. by heating (e.g. about 50° C. to about 150° C., preferably 90° C.) in the presence of Cl(CH$_2$)$_{m+1}$COCl and C$_2$H$_4$Cl$_2$, to form the compounds represented by Formula 17. Compounds of Formula 17 may then be reacted (EQ XA) with a nucleophile X$^-$ (or XH) as discussed above for EQ I, to prepare the compounds represented by Formula 11. Compounds of Formula 17 may also be heated (e.g., at about 50° C. to about 150° C., preferably about 100° C. ) in the presence of an activating agent such as POCl$_3$, and DMF, and then quenched with water (EQ. XB) to prepare the compounds of Formula 8A. In EQ XIB, when n=0 (i.e., no Y substituent), p=0, W is phenyl (C$_6$H$_5$) and m is 1 or 2—see for example, Hayes et al., J.Chem. Res. (Synop), page 414 (1980). The reactions in EQ X and XB may be exemplified by EQ XC and EQ XD as follows:

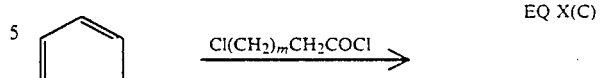

EQ X(C)

(16A)

(17A)

(17A)

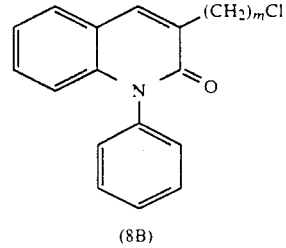
(8B)

EQ X(D)

The compound represented by Formula 17A is reacted with POCl$_3$ and (CH$_3$)$_2$NCHO at elevated temperatures (e.g., 50° C. to 150° C.). The reaction is then quenched with water and the resulting solution is allowed to stand for about 24 hours at room temperature (RT) to form the compounds represented by Formula 8 (see for example, Hayes et al., supra).

When an unsymmetrical diphenylamine starting material is used, a mixture of isomers may result; cyclization will prefer to take place onto the more electron-rich aromatic ring—see EQs XI and XII below.

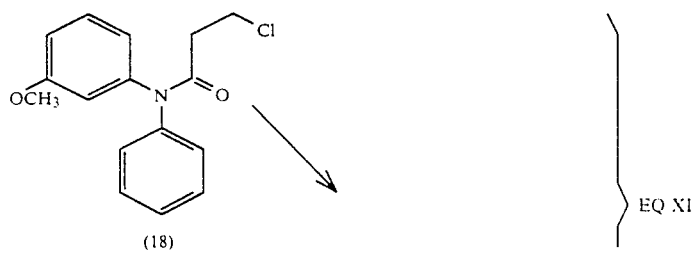
(18)

EQ XI

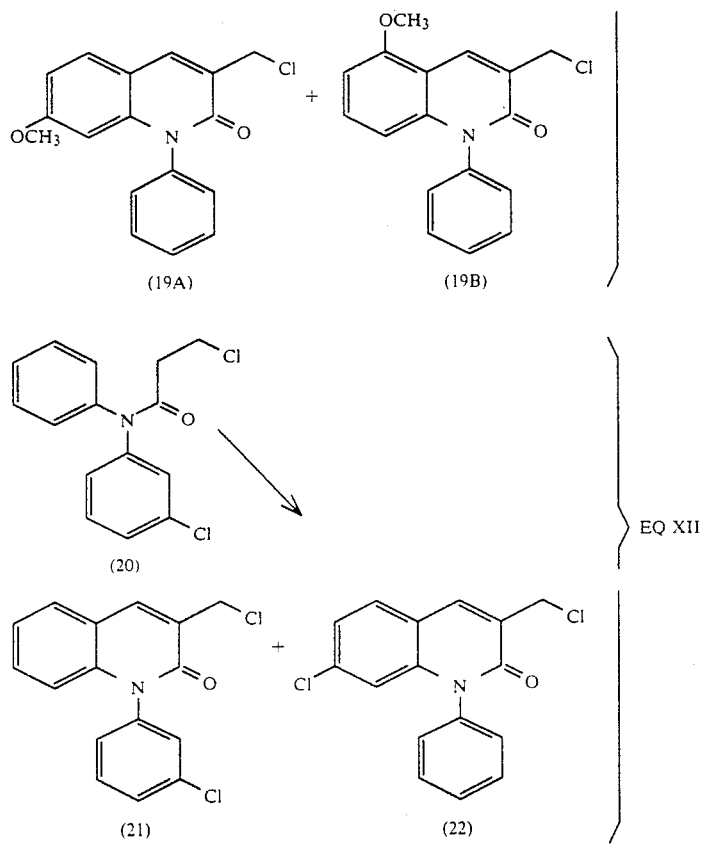

The reaction in EQ XI and EQ XII take place using DMF and $POCl_3$ followed by the addition of water as discussed above for EQ VI The isomer mixtures may be separated by techniques well known in the art, such as chromatography and crystallization.

Conventional electrophilic substitution on 2-quinolone and related compounds may be used to introduce substituents onto the benzenoid ring of the quinolone. A general account of such chemistry can be found in Boulton et al. (Eds.) "Comprehensive Heterocyclic Chemistry", Vol. 2 pages 166–169 and 186–210, specifically Table 10, page 203 (1984) Pergamon Press. In some cases, such as triazolo compounds, this may be carried out after the introduction of the side chain at the number 3 position of the quinolone ring. These processes are exemplified by EQ XIII and XIV as follows:

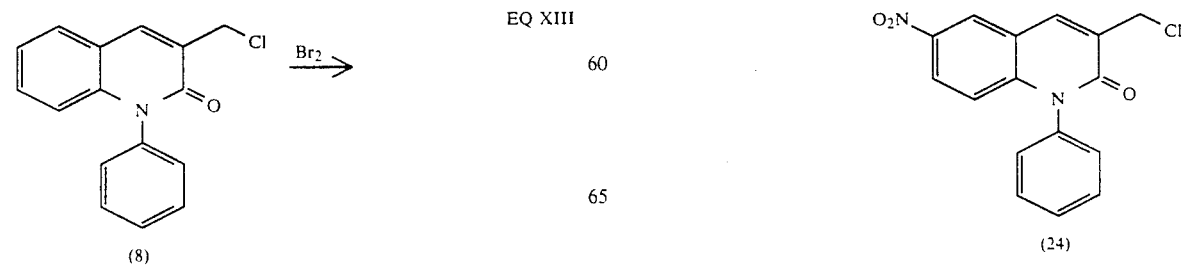

The X-substituent, once introduced, may be modified by known chemistry. For example, see EQs XV and XVI below:

about −10° C. to about 50° C. with about 0° C. being preferred.

Those skilled in the art will appreciate that in reac-

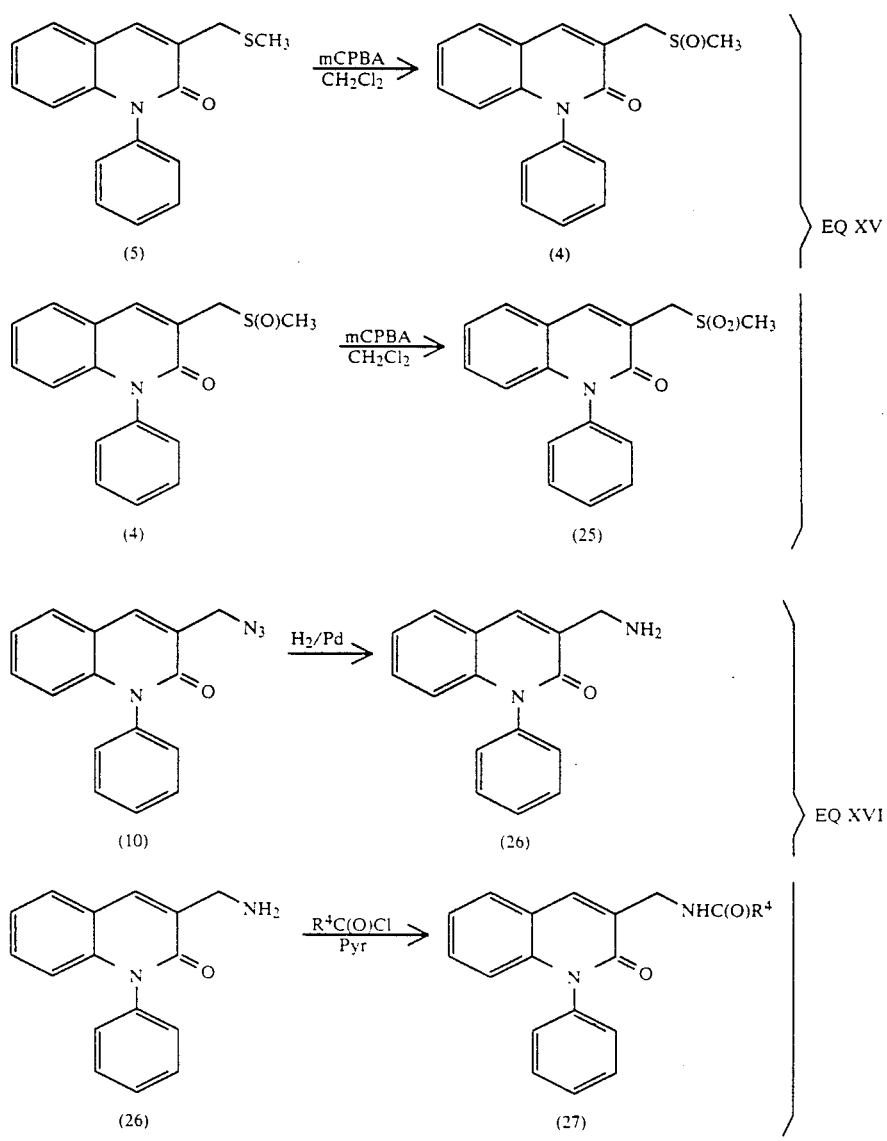

In EQ XV, mCPBA stands for metachloroperoxybenzoic acid. The reactions in EQ XV are usually carried out at a temperature within the range of about −10° C. to about 50° C. and preferably 0° C. In EQ XVI "Pyr" is an abbreviation for pyridine. Also the reaction forming Formula 27 from Formula 26 is usually carried out at a temperature within the range of tions such as those represented by EQs I and II, isomer mixtures may be obtained. The isomer mixtures may be separated by known in the art techniques, such as chromatography and crystallization. For example, when the sodium salt of tetrazole is used, the results that may be obtained are presented in EQ XVII.

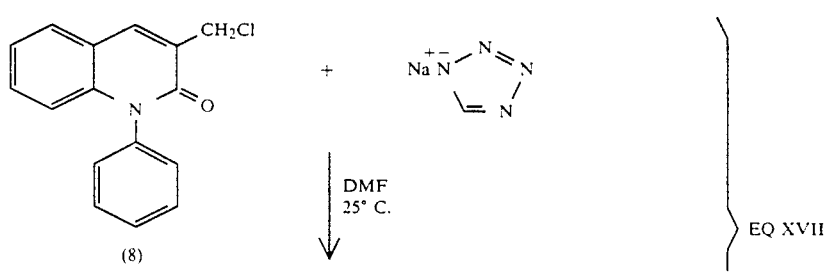

-continued

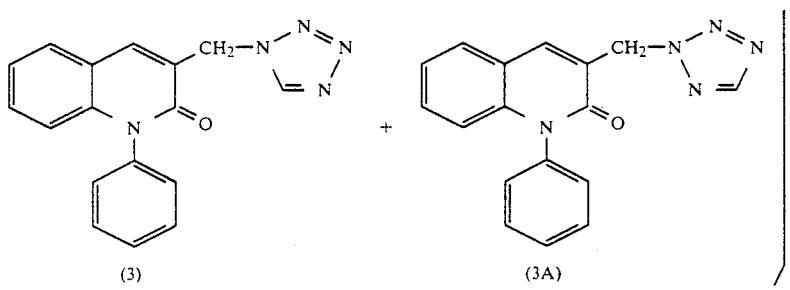

An alternative method to preparing the 1-aryl-3-substituted-2(1H)-quinolones of this invention where m=1 is from an N-aryl-2-aminobenzaldehyde as presented in EQ XVIII.

(1984) for the preparation of quinolones and related compounds from anthranilic acid.

EQ XIX presents a method for preparing compounds represented by Formula 1 wherein X is a heterocycle

EQ XVIII

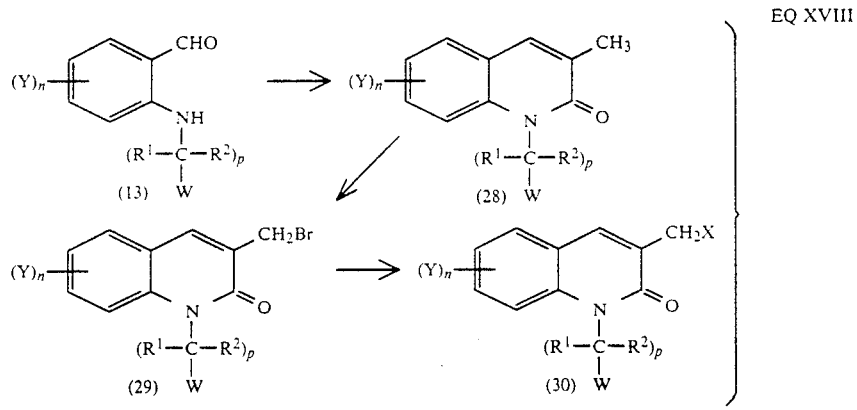

In EQ XVIII a compound represented by Formula 13 is heated in the presence of a propionic acid derivative such as $(C_2H_5CO)_2O$ or $C_2H_5COOC_2H_5$ or in the presence of a base such as $NaOCOC_2H_5$ to form a compound of Formula 28. The compound of Formula 28 is then reacted with a brominating agent, such as N-bromosuccinimide (NBS), to form a compound of Formula 29. The compound of Formula 29 is then reacted with a nucleophile ($X^-$ or XH as discussed in EQ I) to produce a compound of Formula 30. The reactions are all carried out in accordance with known in the art methods. Also see Boulton et al., eds., Comprehensive Heterocyclic Chemistry., volume 2, pages 443-448 bound by one of its ring carbon atoms to the number 3 position of the quinolone ring (Those skilled in the art will appreciate that as used herein, the term "bound to the number 3 position" includes a substituent which is bound through one or more —$CH_2$— groups to the number 3 position of the quinolone).

EQ XIX

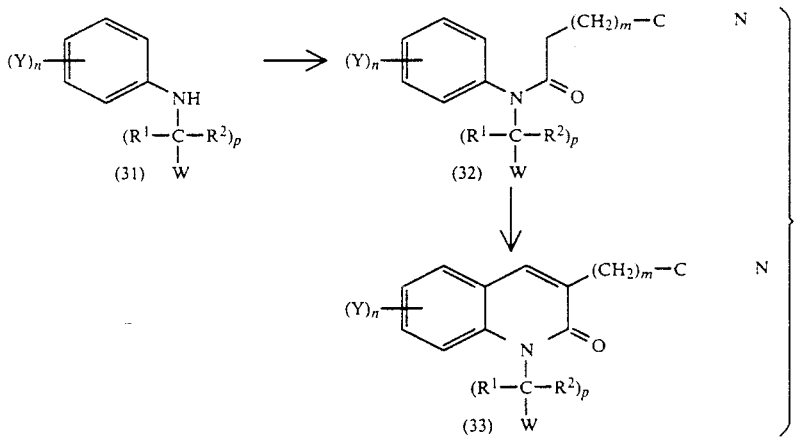

In EQ XIX a compound represented by Formula 31 is reacted with an acid chloride to yield a compound of Formula 32. A compound of Formula 32 is then heated in the presence of DMF and an activating agent such as $POCl_3$, and is then quenched with water to produce a compound represented by Formula 33. Such reactions are known in the art —see for example EQ VI and the references cited in the discussion.

When substituent X in Formula 1 is a heterocycle, the heteroaryl substituted quinolone may be prepared by known methods for example see EQ XX.

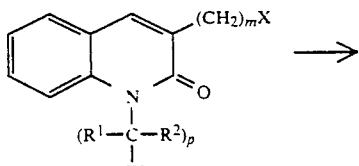

EQ XXII

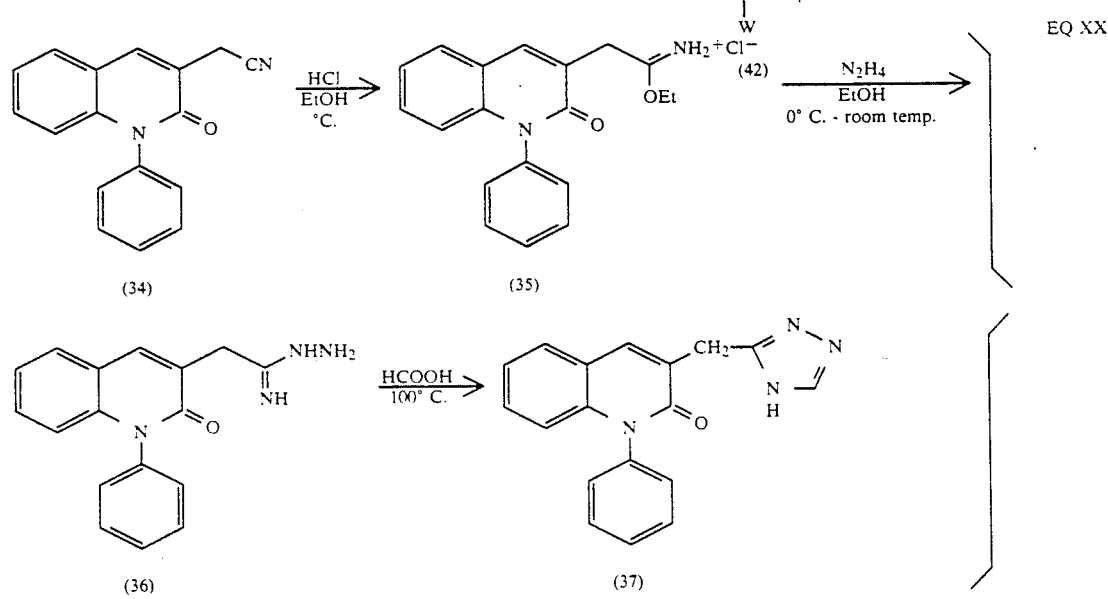

EQ XX

In EQ XX, a compound represented by Formula 34 is reacted with HCl and $C_2H_5OH$ to produce a compound represented by Formula 35. The compound of Formula 35 is then reacted with hydrazine to form a compound represented by Formula 36. The compound of Formula 36 is then reacted with HCOOH or a lower alkyl formate to produce a compound represented by Formula 37.

EQ XXI represents a known in the art sequence of reactions for preparing N-unsubstituted-3-substituted-2-quinolones. See for example, Meth-Cohn et al., J. Chem. Soc. Perkin I, 1520–1530 (1981).

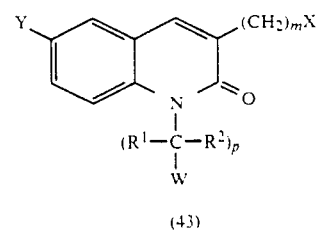

EQ XXI

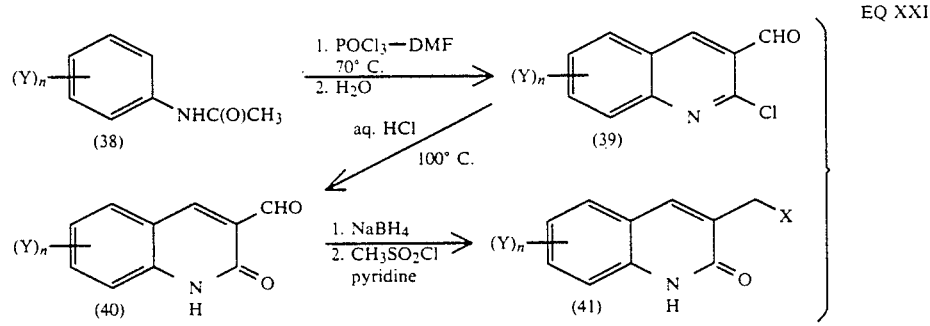

wherein X is $-OSO_2CH_3$.

EQ XXII represents transformation of compounds of Formula 1, wherein n is 0, to other species of compounds of Formula 1 wherein there is an electrophilic group on the benzenoid ring of the quinolone ring.

Thus, by known in the art procedures (see for example "Comprehensive Heterocyclic Chemistry", Vol. 2, pages 166–169 and 186–210 cited supra.) Y substituents (EQ XXII) such as Br, $NO_2$ and $SO_2Cl$ may be placed on the benzenoid ring using their electrophiles $Br_2$, $HNO_3$, and $HClSO_3$, respectively. In this method W should not contain any electron donating groups, such as, $-OCH_3$. This method, however, will not generally be useful for X groups which are sensitive to oxidation, such as —$SCH_3$ and —$S(O)CH_3$ groups. This method is suitable for X groups such as the azoles, e.g. triazole and tetrazole.

EQ XXIII illustrates a method for preparing one species of Formula 1 compounds from another species of Formula 1 compounds.

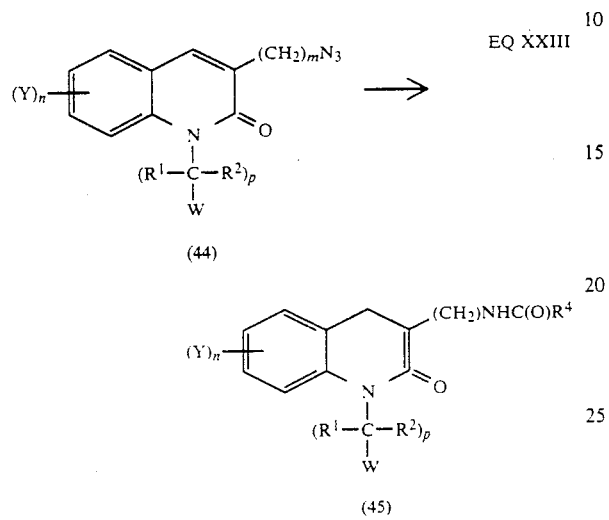

(44)

(45)

The conversion of Formula 44 compounds to Formula 45 compounds is accomplished, as known in the art, by hydrogenating with $H_2$ and Pd, and then acylating with, e.g. $(R^4CO_2)_O$.

EQ XXIV illustrates another method of preparing a 4 substituted-1, 2, 4 triazole from a primary amine.

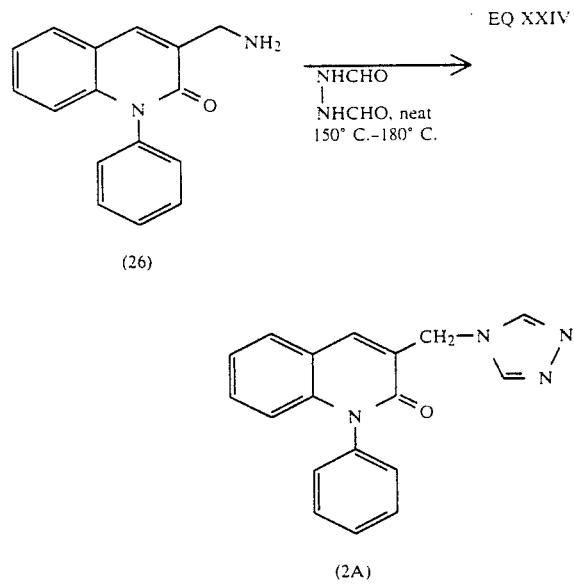

(26)

(2A)

The reaction is carried out by heating (e.g., at about 150° C.) the compound of Formula 26 with CHON(H)N(H)CHO.

EQ XXV also represents a known in the art method of changing the side chain substituent of the substituted quinolone.

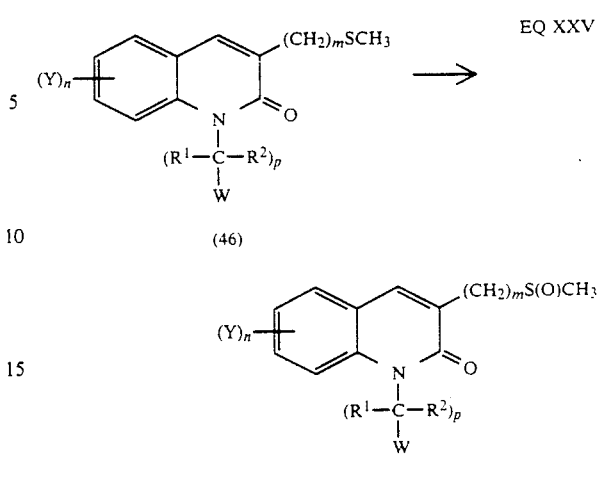

(46)

(47)

The reaction in EQ XXV is carried out using one equivalent of mCPBA in a solvent such as $CH_2Cl_2$.

The compounds of this invention can be used to treat allergies in mammals (e.g., humans) and a preferred use is for treating allergic chronic obstructive lung disease (sometimes referred to as COPD or chronic obstructive pulmonary disease). Chronic obstructive lung disease as used herein means disease conditions in which the passage of air into and out of the lungs is obstructed or diminished such as is the case in asthma, allergic or seasonal rhinitis, and/or bronchitis and the like.

The compounds of this invention affect both 5-lipoxygenase (5-LO) and cyclooxygenase (CO) derived mediators of inflammation. They do not directly inhibit the enzymes. Thus,. the compounds of the invention may thus be used to treat arthritis, bursitis, tendonitis, gout and other inflammatory conditions in mammals (e.g., humans) with an advantage in efficacy and reduced side effects, such as gastrointestinal irritation, which are known to be associated with direct inhibitors of CO such as indomethacin and piroxicam.

The biological activity of classical nonsteroidal anti-inflammatory drugs (NSAID) is attributable to inhibition of the CO pathway which converts arachidonic acid to prostaglandis. In diseases such as rheumatoid arthritis, the NSAIDs have limited efficacy since the cause of rheumatoid arthritis involves more than one mechanism. This hypothesis has been supported by the discovery of proinflammatory leukotrienes including a chemoattractant for neutrophils, leukotriene $B_4$, which is formed from arachidonic acid via the 5-LO pathway. Therefore, a drug that affects both the CO and the 5-LO derived mediators of inflammation may be a superior anti-inflammatory agent.

The compounds of the invention are also useful in the treatment of hyperproliferative skin diseases, e.g., psoriasis, lichenified eczema or seborrhoeic dermatitis in mammals (including humans).

The compounds of this invention do not have the adverse gastrointestinal effects such as those associated with some CO inhibitors.

Representative compounds of Formula 1 include, but are not limited to the compounds represented by Formulas 2, 2A, 3, 4, 5, 6, 9, 10, 25, 26, 27 and 37 described above, as well as Formulas 48 to 98 listed below:

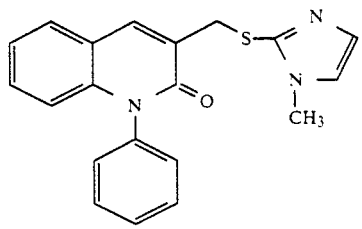 (48)
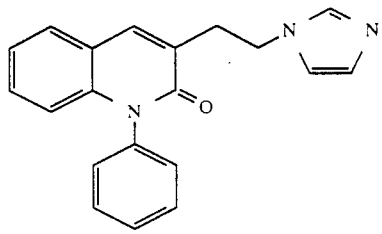 (49)
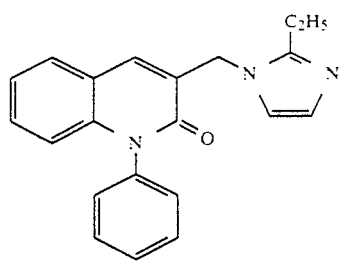 (50)
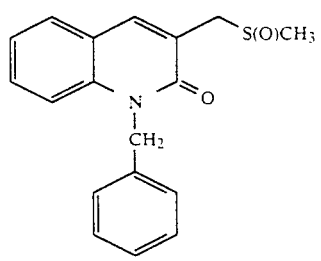 (51)
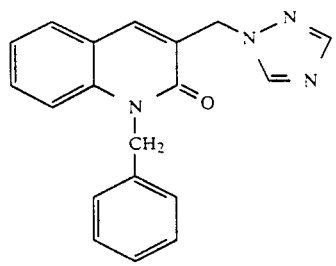 (52)
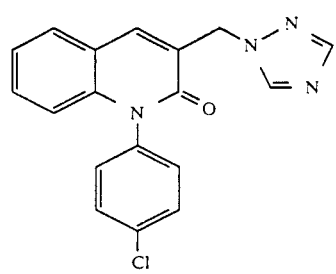 (53)
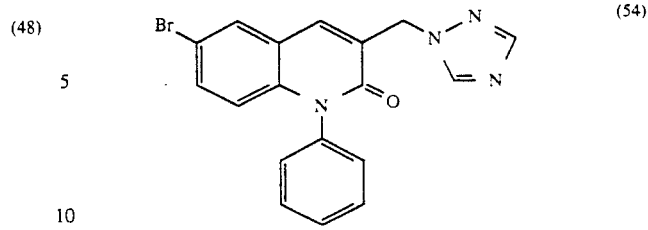 (54)
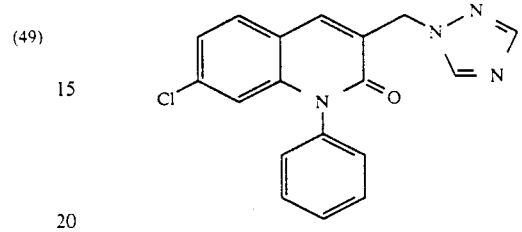 (55)
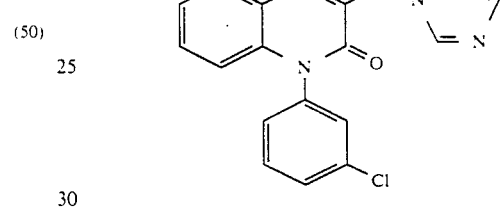 (56)
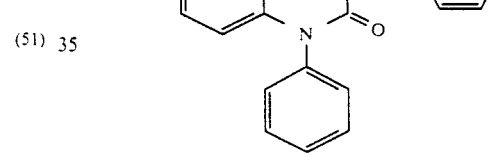 (57)
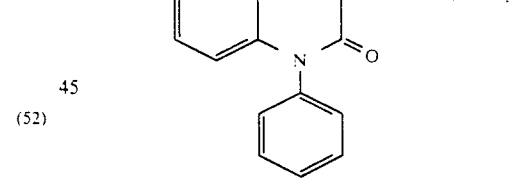 (58)
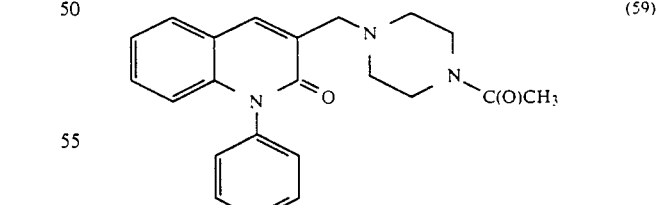 (59)
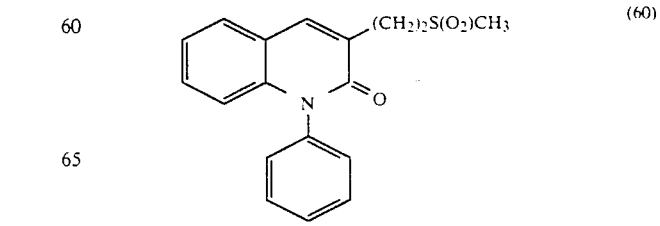 (60)

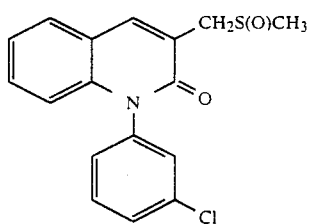 (61)
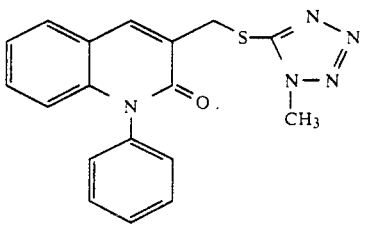 (62)
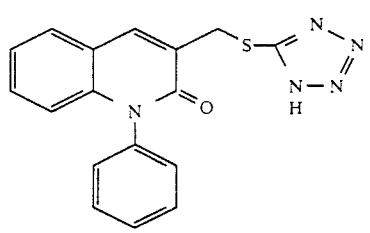 (63)
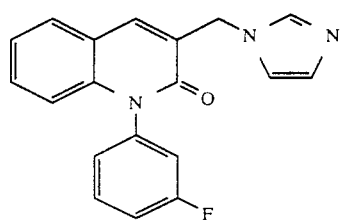 (64)
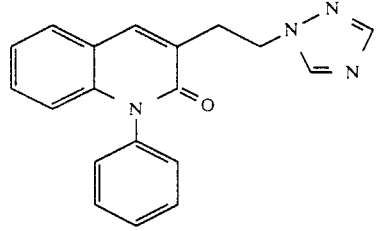 (65)
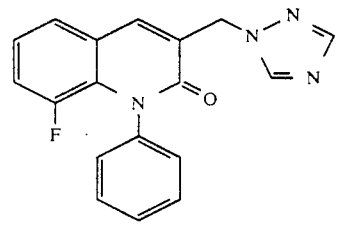 (66)
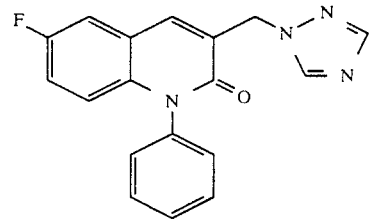 (67)
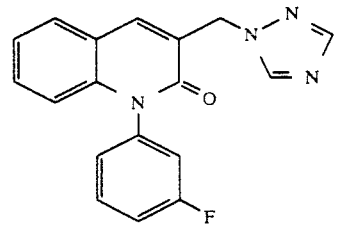 (68)
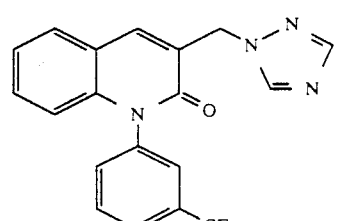 (69)
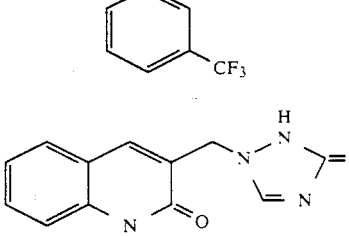 (70)
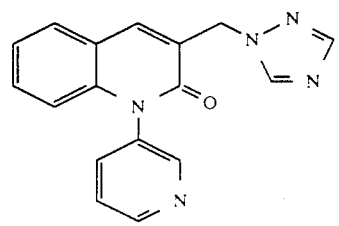 (71)
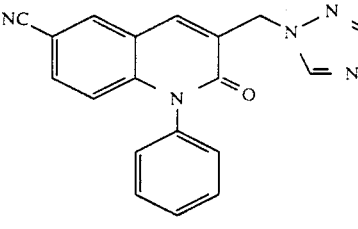 (72)
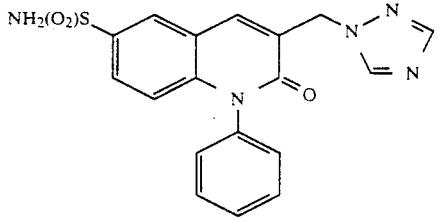 (73)
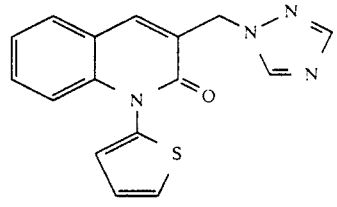 (74)

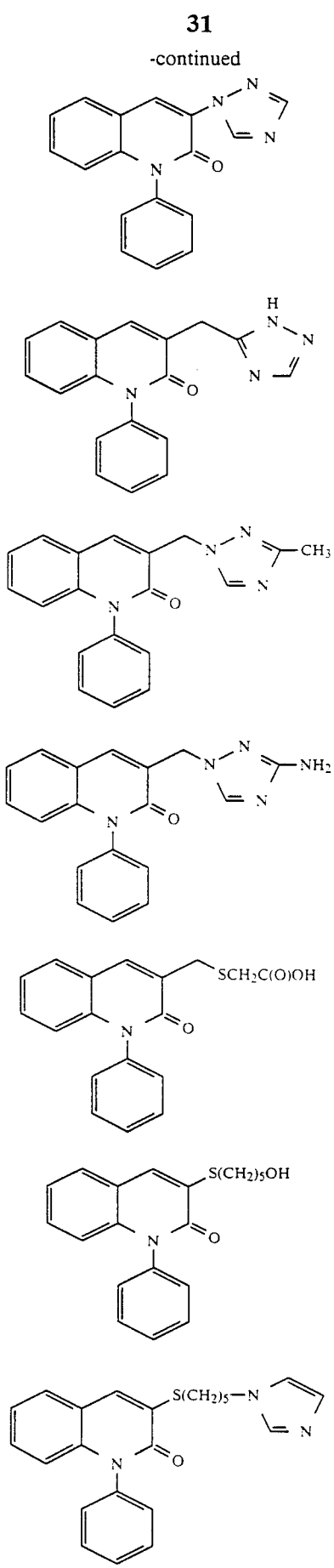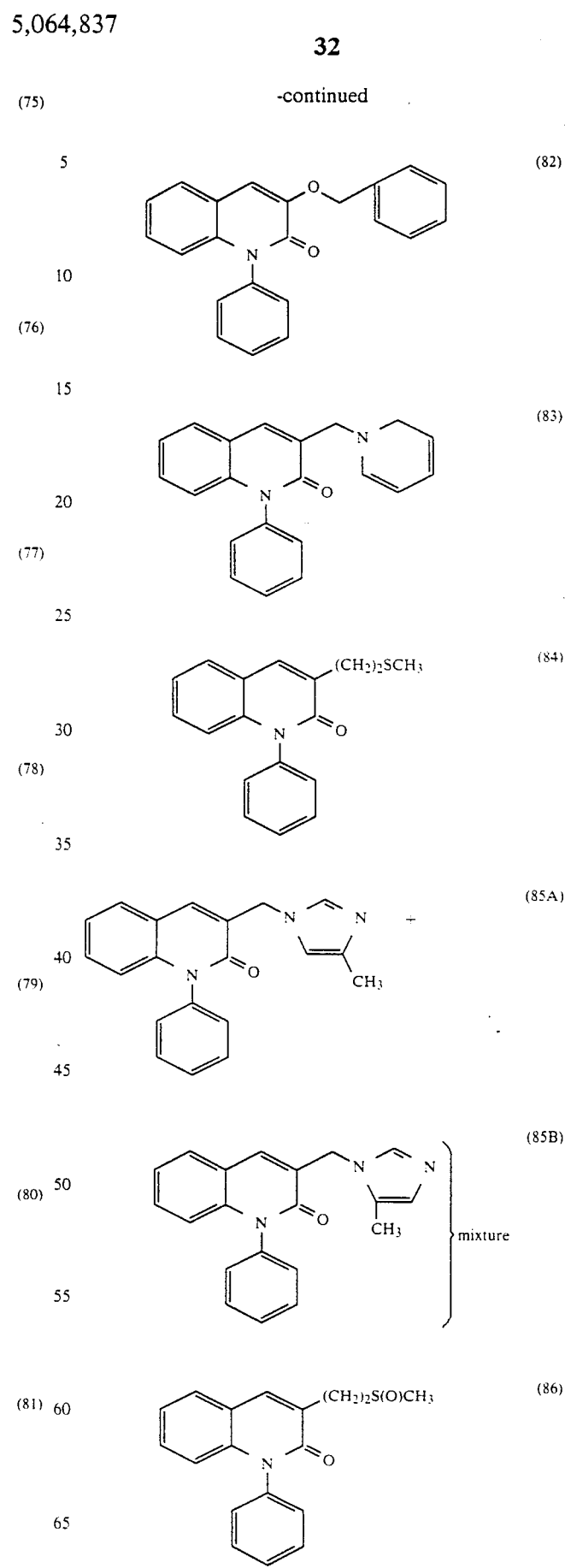

-continued

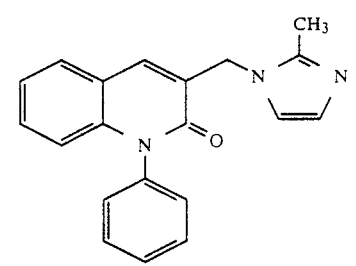 (87)

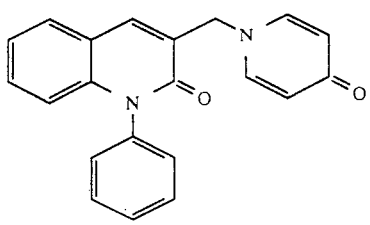 (88)

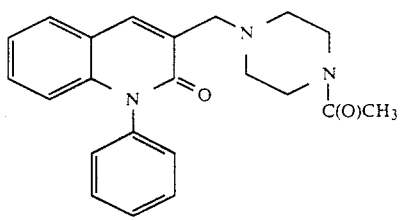 (89)

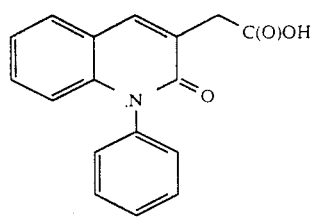 (90)

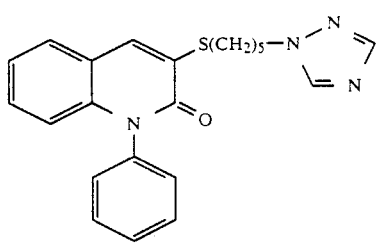 (91)

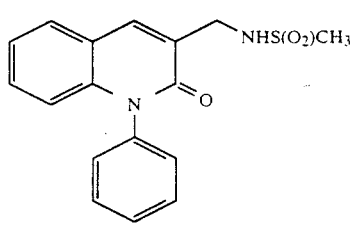 (92)

-continued

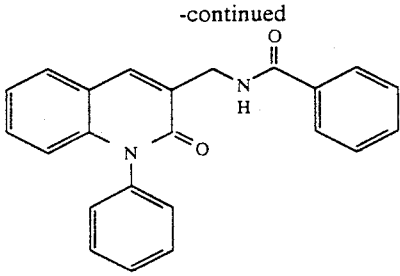 (93)

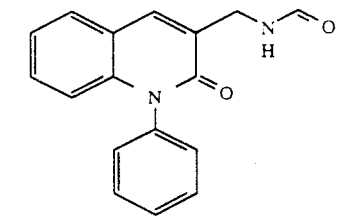 (94)

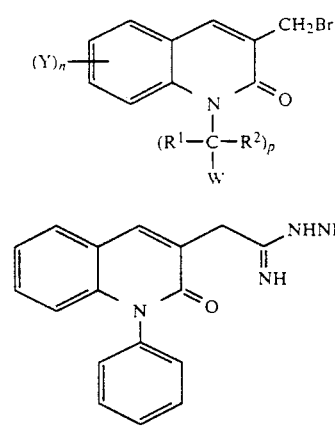 (95)

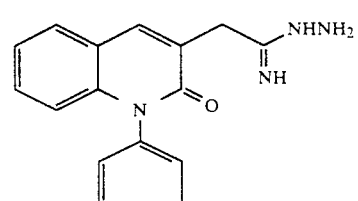 (96)

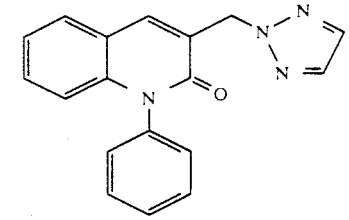 (97)

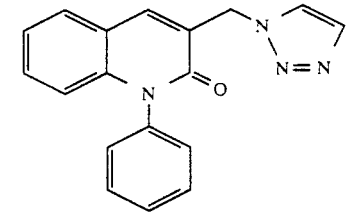 (98)

The compounds of this invention are effective in treating inflammation, allergies and hyperproliferative skin diseases.

The compounds of this invention can be administered in any number of conventional dosage forms. Oral dosage forms are preferred for allergies and inflammation, but can be used for treating hyperproliferative skin diseases. Solid dosage forms include capsules, tablets, pills, powders, suspensions, solutions, cachets or suppositories. Parenteral preparations include sterile solutions or suspensions. Inhalation administration can be in the form of a nasal or oral spray, or by insufflation. Topical dosage forms which are preferred for hyperproliferative skin diseases can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives lubricants, etc.

The compounds of this invention can be formulated into dosage forms suitable for oral, parenteral and topical administration preferably oral by combining them by conventional means with inert, pharmaceutically acceptable carriers which can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablets disintegrating agents; it can also be an encapsulating material. Powders and tablets preferably contain from 5 to about 70 percent by weight of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. Tablets, powders, cachets and capsules can be used as solid dosage forms suitable for the oral route of administration.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application, preferred for use in treating hyperproliferative skin diseases, may include the above liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents. etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides and the like as well as other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The dosages may be varied depending upon the requirements of the patient, the severity of the condition being treated and the particular compound being employed. Determination of the proper dosage for a particular situation is within the skill of the art. For convenience, the total daily dosage may be divided and administered in portions during the day if desired.

In treating allergies, the compounds of this invention may be administered by any conventional mode of administration preferably oral, by employing an antiallergic effective amount of a compound of this invention for such mode. For example, when administered orally they are active at doses of from about 0.5 to about 25 mg/kg of body weight and preferably about 0.5 to about 10 mg/kg; when administered parenterally, e.g., intravenously, the compounds are active at dosages of from about 0.1 to about 5 mg/kg body weight and preferably about 0.1 to about 2.5 mg/kg, and when administered by inhalation (aerosol or nebulizer) the compounds are active at dosages of about 0.1 to about 5 mg per puff, and one to four puffs may be taken every 4 hours. The dosage to be administered and the route of administration depends upon the judgement of the attending clinician considering particular compound used, the age and general health of the patient and the severity of the allergic condition.

The compounds of this invention can be administered by any conventional mode of administration preferably oral, to obtain the anti-inflammatory activity by employing an anti-inflammatory effective amount of a compound of this invention. The compounds of this invention, as an anti-inflammatory agent, may be administered at doses of about 0.5 to about 1000 mg per day, and preferably about 5 to about 500 mg per day. Preferably the total dosages are administered in 2 to 4 divided doses per day. For example, an oral dosage range of from about 5 mg per day to about 500 mg per day in divided doses taken at about 4 hour intervals may be used. The dosage to be administered and the route of administration depends upon the judgment of the attending clinician considering particular compound used, the age and general health of the patient and the severity of the inflammatory condition.

When administered for the treatment of hyperproliferative skin disease, the compounds of this invention may be administered topically, orally, rectally or parenterally, preferably topically although oral administration is effective. When administered topically, the amount of compound administered varies widely with the amount of skin being treated, as well as with the concentration of active ingredient applied to the affected area, thus topical compositions containing about 0.1% to 10.0% by weight of active compound can be used. When administered orally, the compounds of this invention are effective for the treatment of hyperproliferative skin disease at daily doses ranging from about 0.1 mg/kg to about 100 mg/kg of body weight, preferably from about 5 mg/kg to about 50 mg/kg, which may be administered in divided doses. When administered rectally, the compounds of this invention may be administered in daily doses ranging from about 0.1 mg/kg to about 100 mg/kg. When administered parenterally, the compounds of this invention are effective for the treatment of hyperproliferative skin disease in daily doses ranging from about 0.1 mg/kg body weight to about 10 mg/kg body weight which may be administered in divided doses.

As a result of the administration of a compound of this invention, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

In a preferred method of carrying out the invention to treat psoriasis or other hyperproliferative skin diseases, a pharmaceutical formulation comprising a compound of this invention together with a non-toxic, pharmaceutically acceptable topical carrier, usually in concentrations in the range of from about 0.1 percent to about 10 percent by weight, preferably from about 0.1 percent to about 5 percent, is administered until the condition has improved.

The following formulations exemplify some of the dosage forms of the compositions of this invention. In each, the term "active compound" designates compound of formula 2. However, this compound may be replaced by equally effective amounts of other compounds of this invention.

| | Pharmaceutical Dosage Form Examples Example A Tablets | | |
|---|---|---|---|
| No. | Ingredient | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

METHOD OF MANUFACTURE

Mix Item Nos. 1 and 2 in a suitable mixer for 10–15 minutes. Granulate the mixture with Item No. 3. Mill the damp granules through a coarse screen (e.g., ¼", 0,.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

| | Example B Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

METHOD OF MANUFACTURE

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

| Example C Parenteral Preparation | | |
|---|---|---|
| Ingredient | mg/vial | mg/vial |
| Active Compound Sterile Powder | 100 | 500 |

For reconstitution add sterile water for injection or bacteriostatic water for injection.

The following examples are illustrative only and should not be construed as limiting the invention in any way. Those skilled in the art will appreciate that variations are possible which are within the spirit and scope of the appended claims.

The anti-inflammatory and the anti-allergy properties of the compounds of this invention were determined using the following test protocols.

REVERSE PASSIVE ARTHUS PLEURISY REACTION (RPAPR)

RPAPR was produced by a modification of the Yamamoto et al. method (Agents and Actions 5: 374-377, 1975). Thirty (30) minutes prior to lightly anesthesizing rats with ether and then sensitizing them by injecting the animals i.v. with 0.33 mg of bovine serum albumin (BSA) dissolved in 0.2 ml sterile saline, a test compound was administered per os (p.o.) as indicated in Table 1. Thirty minutes later, the rats were again lightly anesthetized and challenged intrapleurally with a rabbit anti-BSA antibody (Organon), containing 1.2 mg antibody protein, dissolved in 0.2 ml sterile saline. Four hours after challenge the rats were sacrificed by $CO_2$ inhalation, their pleural cavities exposed and the exudate harvested. The total volumes of each exudate was recorded and the total number of leukocytes determined using a Coulter Counter ZM.

The exudate were then centrifuged and the supernatants decanted. Four volumes of cold 95% acetone was added for each volume of exudate. One half hour later the samples were again centrifuged for 10 minutes. Immediately after, 5 ml of the supernatant was removed and dried under nitrogen. These samples were kept in a freezer until $LTE_4$ and $TxB_2$ were determined using a radioimmune assay kit from Amersham. The results are given in Table 1 below.

GUINEA PIG BRONCHOSPASM

The anti-allergy activity of the compounds of this invention is identified by tests which measure a compound's inhibition of anaphylactic bronchospasms in sensitized guinea pigs having antigen-induced SRS-A mediated bronchoconstriction. Allergic bronchospasms were measured in actively sensitized guinea pigs by a modification of the procedure of Konzett and Rossler, Arch. Expt. Pathol. Pharmakol., 194, pp. 71-74 (1940). Male Hartly guinea pigs were sensitized with 5 mg ovalbumin injected ip and 5 mg injected sc in 1 ml saline on day 1 and 5 mg ovalbumin injected ip on day 4. The sensitized animals were administered the test compounds, as indicated in Table 2, 3-4 weeks later. To measure anaphylactic bronchospasm, sensitized guinea pigs were fasted overnight and the following morning were anesthetized with 0.9 mL/kg ip dialurethane. The trachea and jugular vein were cannulated and the animals were ventilated by a Harvard rodent respirator. A side arm to the tracheal cannula was connected to a Harvard pressure transducer to obtain a continuous measure of intratracheal pressure. An increase in intratracheal pressure was taken as a measure of bronchoconstriction. Each guinea pig was injected i.v. with 1 mg/kg propranolol, 5 mg/kg indomethacin and 2 mg/kg mepyramine given together in a volume of 1 mL/kg. Fifteen minutes later, the animals were challenged with antigen (0.5 percent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge. The results are given in Table 2 below.

SRSA RELEASE IN VITRO

First, kill sensitized guinea pigs by a blow to the head, remove the lungs and clean them of visible connective tissue, trachea and large blood vessels. Slice the lungs from individual animals into fragments approximately 1 mm in thickness using a McIlwain tissue chopper and wash them with oxygenated Tyrode's buffer. Transfer weighted allquots (approximately 400 mg wet weight) of lung into vials containing 2 ml of fresh Tyrode's solution (containing 10 mM cysteine) and incubate in the presence or absence of test compound for 12 minutes at 37° C., challenge the tissues with 20 µg ovalbumin/ml (final concentration) and incubate for 15 minutes.

To measure leukotriene release, extract an aliquot of supernatant fluid with 4 volumes of 100% ethanol. After removal of the precipitated protein, dry the clear fluid under a stream of $N_2$ gas. Measure the leukotriene content by a radioimmunoassay using $[^3H]LTC_4$ (leukotriene $C_4$) and antiserum obtained from New England Nuclear. Calculate percent inhibition of leukotriene release by comparing for each lung the release in the presence of the test compound to that in the absence of test compound. The results are given in Table 2 below.

TABLE 1
RAT PLEURAL CAVITY

| Example | Formula | Dose (mg/kg. p.o.) | Rat Pleural Cavity % Inhibition | | | |
|---|---|---|---|---|---|---|
| | | | Cells | Fluid | $LTE_4$ | $TxB_2$ |
| 1 | 4 | 25 | 80 | 79 | 73 | 85 |
| 2 | 48 | 25 | 75 | 40 | 57 | 67 |
| 3 | 6 | 25 | 85 | 88 | 100 | 100 |
| 4 | 49 | 25 | 86 | 53 | — | — |
| 5 | 3 | 10 | 75 | 50 | 61 | 77 |
| 6 | 50 | 25 | <10 | <10 | — | — |
| 7 | 2 | 5 | 64 | 42 | 53 | 67 |
| 8 | 51 | 25 | 22 | <10 | — | — |
| 9 | 52 | 25 | 44 | 46 | — | — |
| 10 | 53 | 25 | <10 | 18 | — | — |
| 11 | 54 | 25 | <10 | <10 | — | — |
| 12 | 55 | 25 | <10 | <10 | — | — |
| 13 | 56 | 5 | 56 | 63 | — | — |
| 14 | 57 | 25 | 20 | 19 | — | — |
| 15 | 10 | 25 | 61 | 78 | 96 | 99 |
| 16 | 58 | 25 | 62 | 53 | — | — |
| 17 | 59 | 25 | 68 | 68 | — | — |

$LTE_4$ = Leukotriene $E_4$ - a measure of lipoxygenase (LO) derived mediators of inflammation.
$TxB_2$ = Thromboxane $B_2$ - a measure of cyclooxygenase (CO) derived mediators of inflammation.

The data in Table 1 show that the compounds of this invention exert an anti-inflammatory action in the described test. The test described is known to be predictive of anti-inflammatory activity in humans and other mammals.

TABLE 2
SRSA RELEASE AND GUINEA PIG. BRONCHOSPASM

| Example | Formula | SRSA Release in vitro | | G.P. Bronchospasm | |
|---|---|---|---|---|---|
| | | Dose (uM) | % I | Dose (mg/kg. p.o.) | % I |
| 18 | 4 | 30 | 76 | 1.5 | 51 |
| 19 | 3 | 30 | 83 | 1.5 | 49 |
| 20 | 2 | 30 | 83 | 1.5 | 54 |
| 21 | 53 | 30 | 76 | 5 | 18 |

The data in Table 2 show that compounds of this invention inhibit release of SRS-A (slow reacting substance of anaphylaxis) in vitro and also inhibit SRS-A mediated bronchoconstriction) in an animal model of allergic bronchrospasm. The test is knowing to be predictive of activity in humans and other mammals.

EXAMPLE 22

Preparation of 1-Phenyl-3-(1H-1, 2, 4-Triazol-1-Ylmethyl)-2(1H)-Quinolone and 1-Phenyl-3-(4H-1, 2, 4-Triazol-4-Ylmethyl)-2(1H)-Quinolone See Equation II for depiction of reaction scheme. To hexane-washed sodium hydride (from 10 gm of 60% dispersion) stirred in dimethyl formanide (DMF) (600 mL) add in portions 1, 2, 4-triazole (19 gm). Stir at 25° C. for 0.5 h, add 1-phenyl-3-chloromethyl-2(1H)-quinolone (59 gm) and stir at 25° C. for 18 hours. Add methanol (10 mL) followed by water (1200 mL), filter off, wash with water and dry the mixture of (2) and (2A). Chromatograph on silica gel, eluting with a gradient of 0.5 to 20% methanol-dichloromethane to elute first the major compound (2), followed by (2A).

In each case, evaporate the pure eluates and triturate the solid with ether, filter and dry at 50° C. in high vacuum.

Compound (2), 1-Phenyl-3-(1H-1,2,4-triazol-1-ylmethyl)-2(1h)-quinolone
mpt 203°–205° C.
DMR (CDCl$_3$), $\delta = 5.39$ (s,2), 6.67 (d,1), 7.1–7.7 (m,8), 7.80 (s,1), 7.98 (s,1) and 8.39 (s,1).
Compound (2A), 1-Phenyl-3-(4H-1,2,4,-triazol-4-ylmethyl)-2(1H)-quinolone
mpt 211°–213° C.
PMR (CDCl$_3$), $\delta = 5.17$ (s,2), 6.60 (d,1), 7.0–7.8 (m,9) and 8.33 (s,2).

EXAMPLE 23

Preparation of 1-Phenyl-3-(1H-Tetrazol-1-Ylmethyl)-2(1H)Quinolone and 1-Phenyl-3-(2H-Tetrazol-2-Ylmethyl)-2(1H)-Quinolone See Equation XVII for depiction of reaction scheme.

Following the procedure of example 22, react the chloro compound with sodium tetrazole in dimethylformamide, at 25° C. for 18 h. Dilute the reaction with water, extract with dichloromethane, wash the extracts 3× with water and evaporate. Chromatograph on silica gel using a gradient of ethyl acetate in dichloromethane to obtain as the less polar compound (3) and the more polar compound (3A).
(3), 1-phenyl-3-(1H-1-Tetrazol-1-ylmethyl)-2(1H)Quinolone
mpt 183°–185° C.
PMR (CDCl$_3$), $\delta = 5.91$ (s,2), 6.70 (d,1), 7.1–7.7 (m,8) and 8.62 (s,1).
(3A), 1-Phenyl-3-(2H-Tetrazol-2-ylmethyl)-2(1H)quinolone
mpt 182°–183° C.
PMR (CDCl$_3$), $\delta = 5.62$ (s,2), 6.68 (d,1), 7.2–7.7 (m,8), 8.04 (s,1) and 9.00 (s,1).

EXAMPLE 24

Preparation of 1-Phenyl-3-Methylthiomethyl-2(1H)-Quinolone

Compound (8) + NaSCH$_3$ → Compound 5.

Following the procedure of example 22, react the chloro-compound with sodium thiomethoxide in methanol at room temperature for 2 hours. Dilute with water, extract with dichloromethane, dry and evaporate, and recrystallize from dichloromethane-hexane to give 1-Phenyl-3-Methylthiomethyl-2(1H)-Quinolone.
mpt 138°–140° C.
PMR (CDCl$_3$), $\delta = 2.18$ (s,3), 3.75 (s,2), 6.66 (d,1), 7.1–7.7 (m,8) and 7.85 (s,1).

EXAMPLE 25

Preparation of 1-Phenyl-3-(Azidomethyl)-2(1)-Quinolone

See Equation V for a depiction of the reaction scheme.

Following the procedure of example 22, react the chloro compound with excess sodium azide in dimethyl-sulfoxide at 25° C. for 18 hours. Dilute, extract and wash the dichloromethane extract with water, dry, evaporate and crystallize from ether to obtain 1-Phenyl-3-(Azidomethyl)-2(1H)-Quinolone.
mpt: decomposes at 150° C.
PMR (CDCl$_3$), $\delta = 4.47$ (s,2), 6.67 (d,1) and 7.1–7.7 (m,8) and 7.87 (s,1).

EXAMPLE 26

Preparation of 1-Phenyl-3-(1H-Imidazol-1-Ylmethyl)-2(1H)-Quinolone

See Equation III for a depiction of the reaction scheme.

Following the procedure of example 22, react the chloro compound with the sodium salt of imidazole in tetrahydrofuran at room temperature or with a large excess of free imidazole in refluxing tetrahydrofuran. Dilute with dichloromethane, dry and evaporate, and chromatograph on silica gel with a gradient of methanol in dichloromethane to obtain 1-Phenyl-3-(1H-Imidazol-1-ylmethyl)-2(1H)-Quinolone as a white solid.
mp: 111°–113° C.
PMR (CDCl$_3$), $\delta = 5.17$ (s,2), 6.67 (d,1) and 7.0–7.7 (m,12)

EXAMPLE 27

Preparation of 1-Phenyl-3-(4-Acetylpiperazin-1-Ylmethyl)-2(1H)-Quinolone

Compound (8) + 1-acetylpiperazine → Compound (89)

Following the procedure of example 22, react the chloro compound with excess 1-acetylpiperazine in dimethylsulfoxide at 25° C. for 18 hours. Add water, filter the product, wash with water and dry at 50° C. in high vacuum to a white powder, 1-Phenyl-3-(4-Acetylpiperazin-1-ylmethyl)-2(1H)-Quinolone.
mp 193°–195° C.
PMR (CDCl$_3$), $\delta = 2.08$ (s,3), 2.4–2.7 (m,4), 3.4–3.9 (m,6), 6.65 (d,1), 7.1–7.7 (m,8) and 7.85 (s,1).

EXAMPLE 28

Preparation of 1-Phenyl-3-(1-Methyl-1H-Imidazol-2-Ylthiomethyl)-2(1H)-Quinolone

Compound (8) + 1-methyl-2-mercaptoimidazole → Compound (48)

React the chloro compound with the sodium salt of 1-methyl-2-mercaptoimidazole to obtain 1-Phenyl-3-(1-Methyl-1H-imidazol-2-ylthiomethyl)-2(1H)-quinolone.

EXAMPLE 29

Preparation of
1-Benzyl-3-(1H-1,2,4-Triazol-1-Ylmethyl)-2(1H)-Quinolone 1-benzyl-3-chloromethyl-2(1H)-quinolone + sodium
1,2,4,-triazole → Compound (95)

React 1-benzyl-3-chloromethyl-2(1H)-quinolone with the sodium salt of 1,2,4-triazole in DMF at 25° C. for 18 hours, following the procedure of example 22. Chromatograph the crude product using 5% methanol-dichloromethane to obtain the major product, 1-Benzyl-3-(1H-1,2,4-triazol-1-ylmethyl-2(1H)-Quinolone.

EXAMPLE 30

Preparation of
1-(3-Chlorophenyl)-3-(1H-1,2,4,-Triazol-1-Ylmethyl)-2(1H)-Quinolone Compound (21) → Compound (56)

Following the procedure of example 22, react 1-(3-chlorophenyl)-3-chloromethyl-2(1H)-quinolone with sodium triazole in dimethylformamide. Chromatograph to obtain the major product, 1-(3-Chlorophenyl)-3-(1H-1,2,4-Triazol-1-ylmethyl)-2(1H)-Quinolone.

EXAMPLE 31

Preparation of
1-Phenyl-7-Chloro-3-(1H-1,2,4-Triazol-1-Ylmethyl)-2(1H)-Quinolone Convert
7-chloro-1-phenyl-3-chloromethyl-2(1H)-quinolone to compound (55)

Following the procedure of example 22, react 7-chloro-1-phenyl-3-chloromethyl-2(1H)-quinolone with sodium triazole in DMF. Chromatograph to obtain the major product, 1-phenyl-7-chloro-3-(1H-1,2,4-triazol-1-ylmethyl)-2(1H)-quinolone.

EXAMPLE 32

Preparation of
1-Phenyl-8-Fluoro-3-(1H-1.2.4,-Triazol-1-Ylmethyl)-2(1H)-Quinolone 8-fluoro-1-phenyl-3-bromomethyl-2(1H)-quinolone → Compound (66)

Following the procedure of example 22, react 8-fluoro-1-phenyl-3-bromomethyl-2(1H)-quinolone with sodium triazole in dimethylformamide. Chromatograph to obtain the major product, 1-phenyl-8-fluoro-3-(1H-1,2,4-triazol-1-yl-methyl)-2-(1H)quinolone.

Preparation of
1-Phenyl-3-Aminomethyl-2(1H)-Quinolone

See Equation XVI for a depiction of the reaction scheme.

Shake a solution of the azido compound produced in example 25 (5 g) and 10% palladium on carbon (1 g) in tetrahydrofuran (100 mL) at 25° C. for 4 hours in hydrogen (60 psi). Filter and evaporate. Dry the residue at 50° C. in vacuum to obtain an amorphous powder, 1-phenyl-3-aminomethyl-2(1H)-quinolone.

PMR (CDCl$_3$), δ=2.05 (s,2, exch. D$_2$O), 3.89 (s,2), 6.66 (d,1), 7.1-7.7 (m,8) and 7.80 (s,1).

EXAMPLE 34

1-Phenyl-3-(Methane Sulfonyl Amino Methyl)-2(1H)-Quinolone

Compound (26) → Compound (92)

Stir a solution of the amine from example 33 (0.5 g) in dichloromethane (10 ml) and pyridine (1 ml) at 0°-5° C. and add methane sulfonyl chloride (0.2 ml) in dichloromethane (5 ml) over 0.5 hour. Stir at 0°-5° C. for a further 0.5 hour, dilute with dichloromethane and wash with 1N-hydrochloric acid followed by 1N-sodium bicarbonate solution. Dry, evaporate and chromotograph on silica gel with a gradient of ethyl acetate in dichlormethane to obtain the major product. Triturate with ether to crystallize, obtaining 1-phenyl-3-(methanesulfonylaminomethyl)-2(1H)-quinolone.

mpt 173°-175° C.

PMR (CDCl$_3$), δ=2.97 (s,3), 4.34 (s,2), 5.6 (br.s,1, exch. by D$_2$O), 6.73 (d,1), 7.2-7.8 (m,8) and 7.95 (s,1).

EXAMPLE 35

Preparation of
1-Phenyl-3-(Acetamidomethyl)-2(1H)-Quinolone

See Equation XVI for a depiction of the reaction scheme.

Following the procedure of example 34, replacing methanesulfonyl chloride with acetic anhydride, obtain 1-phenyl-3-(acetamidomethyl)-2(1H)-quinolone.

mp 165°-167° C.

PMR (CDCl$_3$), δ=2.00 (s,3), 4.47 (d,2), 6.7 (br.d,.2, 1H exch. by D$_2$O), 7.1-7.8 (m,8) and 7.90 (s,1).

EXAMPLE 36

Preparation of
1-Phenyl-3-(Formamidomethyl)-2(1H)-Quinolone

Compound (26) + N,N'-diformylhydrazine →
Compound (2A) + Compound (96)

Heat in an oilbath at 180°-190° C. for 2 hours a mixture of the amine from example 33 and excess of N,N'-diformylhydrazine. Allow to cool, then shake with water and dichloromethane. Evaporate the organic phase and chromatograph the residue on silica gel, using a gradient of methanol in dichlormethane to obtain the triazole, identical with material isolated as the minor product in example 22, and 1-phenyl-3-(formamidomethyl)-2-(1H)-quinolone.

EXAMPLE 37

Preparation of
1-Phenyl-3-(Methanesulfinylmethyl)-2-(1H)-Quinolone

See Equation XV(step 1) for a depiction of the reaction scheme.

Stir a solution of the methylthiocompound (2.81 g), prepared as described in example 24, in dichlormethane (50 mL) at 0°-5° C. and add dropwise a solution of 85% m-chloroperoxybenzoic acid (2.10 g) in dichloromethane (20 mL) and ether (5 mL). Stir for 2 hours at 0°-5° C. then stir for 0.5 hour at 25° C. with 1N sodium bicarbonate solution (50 ml). Separate the organic phase, dry over magnesium sulfate and evaporate. Crystallize from dichloromethane-hexanes to obtain a white solid, 1-phenyl-3-(methanesulfinylmethyl)-2(1H)-quinolone.

mp 179°-180° C.

PMR (CDCl$_3$)δ=2.62 (s,3), 4.06 (AB system, 2, J=14 Hz), 6.67 (d,1), 7.1-7.7 (m,8) and 7.79 (s,1).

EXAMPLE 38

Preparation of
1-Phenyl-3-(Methanesulfonylmethyl)-2-(1H)-Quinolone

Compound (5) → Compound (25)

Following the procedure of example 37, react the methylthio compound with 2.25 equivalents of m-chloroperoxybenzoic acid in dichloromethane, and allow the reaction to proceed for 6 hours at 25° C. Wash by stirring with an aqueous solution 1N in sodium bicarbonate and sodium sulfite, dry, evaporate and crystallize with ether-hexane to obtain 1-phenyl-3-(methanesulfonylmethyl)-2-(1H)-quinolone.

This is identical with a sample prepared by the general procedure of example 22, reacting the chloro compound with sodium methanesulfinate in refluxing ethanol.

EXAMPLE 39

Preparation of
6-Bromo-1-Phenyl-3-(1H-1,2,4-Triazol-1-Ylmethyl)-2(1H)-Quinolone

Compound (2) → Compound (54)

Reflux for 24 hours a solution of the triazole (1.0 g), prepared according to example 22, bromine (0.5 mL) and anhydrous ferric chloride (0.25 g) in 1,2-dichloroethane (20 mL). Cool, dilute with dichloromethane and wash with 5% sodium sulfite solution. Dry and evaporate, and recrystallize from ethanol-water to obtain 6-bromo-1-phenyl-3-(1H-1,2,4-triazol-1-ylmethyl)-2(1H)-quinolone, mp 237°–240° C.

EXAMPLES OF PREPARATION OF INTERMEDIATES

EXAMPLE 40

Preparation of
1-Phenyl-3-Chloromethyl-2(1H)-Quinolone

Diphenylamine + 3-chloropropionyl chloride →
Compound (8)

Reflux a solution of diphenylamine (51 g) in 1,2-dichloroethane (150 mL) with 3-chloropropionyl chloride (40 mL) for 2 hours. Cool to 40°–50° C. and add over 15 minutes a solution previously made by dropwise addition of dimethylformamide (60 mL) to re-cooled phosphoryl chloride (160 mL).

After the addition, heat the mixture slowly to reflux, and reflux for 3 hours.

Add to a stirred mixture of iced water (1.5 L) and dichloromethane (500 mL), and continue stirring for 18 hours. Extract 2× with dichloromethane and was the combined extracts 2× with water. Dry over $MgSO_4$ and filter.

Pass the filtrate through a pad containing 100 g of silica gel and wash with 5% ether-dichloromethane. Evaporate the combined filtrates and triturate the residue with a small volume of ether-hexane (1:1). Filter and dry the solid to give 1-phenyl-3-chloromethyl-2(1H)-quinolone.

EXAMPLE 41

Preparation of
1-Phenyl-3-(2-Chloroethyl)-2(1H)-Quinolone

Diphenylamine + 4-chlorobutyryl chloride → Title compound

Follow the procedure of example 40, replacing 3-chloropropionyl chloride with 4-chlorobutyryl chloride, to obtain 1-phenyl-3-(2-chloroethyl)-2(1H)-quinolone.

EXAMPLE 42

Preparation of Preparation of
1-Phenyl-3-(1-Chloroethyl)-2(1H)-Quinolone

Diphenylamine + 3-chlorobutyryl chloride → Title Compound

Follow the procedure of example 40, replacing 3-chloropropionyl chloride with 3-chlorobutyryl chloride, to obtain 1-phenyl-3-(1-chloroethyl)-2(1H)-quinolone.

EXAMPLE 43

Preparation of
1-Benzyl-3-(Chloromethyl)-2(1H)-Quinolone $PhNHCH_2Ph \rightarrow PhN(CH_2Ph)(COC_2H_4Cl) \rightarrow$ Title Compound Add 3-chloropropionyl chloride (1.1 eq) to an ice-cooled solution of N-benzylaniline (1.0 eq) and pyridine (1.2 eq). Stir at 0.5° C. for 1 hour, wash with 1N-hydrochloric acid and water, dry, and evaporate to obtain the intermediate amide.

To this material add a pre-formed mixture of dimethylformamide (3 eq) and phosphoryl chloride (7 eq). Heat slowly to 100° C., maintain this temperature for 3 hours, add to excess ice-water and complete the preparation as in example 40. After filtering through silica gel, recrystallize from ether-hexanes to obtain 1-benzyl-3-chloromethyl-2(1H)-quinolone.

EXAMPLE 44

Preparation of
1-(3-Chlorophenyl)-3-Chloromethyl-2(1H)-Quinolone
and
1-Phenyl-7-Chloro-3-Chloromethyl-2(1H)-Quinolone 3-chloro diphenylamine → Compound
(21) + Compound (22)

Follow the procedure of example 40, replacing diphenylamine with 3-chloro diphenylamine. After the same workup, separate the mixture by flash chromatography on silica gel with 0.25% ether-dichloromethane.

Recrystallize each component from ethanol to obtain 1-(3-chlorophenyl)-3-chloromethyl-2(1H)-quinolone, and 1-phenyl-7-chloro-3-chloromethyl-2(1H)-quinolone.

EXAMPLE 45

Preparation of
1-Phenyl-8-Fluoro-3-Bromomethyl-2(1H)-Quinolone

Reflux a solution of 1-phenyl-8-fluoro-3-methyl-2(1H)-quinolone (0.54 g), N-bromosuccinimide (0.38 g) and benzyl peroxide (0.04 g) in dry benzene (11 mL) for 6 hours. Evaporate, partition between dichloromethane and water, dry and evaporate the organic phase, and dry the residue at room temperature and high vacuum to obtain 1-phenyl-8-fluoro-3-bromomethyl-2(1H)-quinolone, suitable for further reactions (see example 32).

EXAMPLE 46

Preparation of 1-Phenyl-8-Fluoro-3-Methyl-2(1H)-Quinolone

Stir a mixture of the hydroxyquinolone (0.92 g) and triethylamine (1.06 mL) in dichloromethane to give a solution, cool to 0° C. and add trifluoromethane sulfonic anhydride (0.58 ml) dropwise. After 10 minutes, wash with aqueous tartaric acid solution and chromatograph on silica gel using 4:1 hexane-ethyl acetate. Evaporate the pure fractions to obtain the intermediate triflate (0.74 g)

Stir a solution of the triflate compound (0.70 g) in ethyl acetate (15 mL) and pyridine (0.19 mL) with 10% palladium on carbon (0.17 g) in a hydrogen atmosphere for 16 hours.

Filter and wash with ethyl acetate. Wash the solutions with dilute hydrochloric acid (1M) and water, dry over magnesium sulfate and evaporate to obtain the product (0.42 g), 1-phenyl-8-fluoro-3-methyl-2(1H)-quinolone, mp 171°–173° C.

EXAMPLE 47

Preparation of 1-Phenyl-3-Chloromethyl-6-Nitro-2(1H)-Quinolone

Stir a solution of the chloro compound (0.27 g) in glacial acetic acid (3.5 mL) and add 90% nitric acid (0.4 mL) followed by concentrated sulfuric acid (0.4 mL), stir for 2 hours, add water, extract with dichloromethane, wash with water, dry and evaporate. Isolate the new compound by preparative TLC (5% ether-dichloromethane on silica gel) and crystallize from ether-hexanes to give 1-phenyl-3-chloromethyl-6-nitro-2(1H)-quinolone, mp 152°–154° C.

The invention being thus described, it will be obvious that the same may be varied in many ways. Such variations are not to be regarded as a departure from the spirit and scope of the invention and all such modifications are intended to be included within the scope of the claims.

What is claimed is:

1. A compound represented by formula 1: wherein the heteroatom or heteroatoms in said heteroaryl must be nitrogen and wherein said heteroaryl is

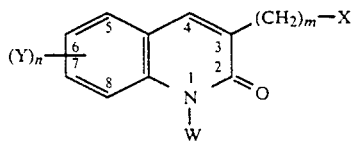

or a pharmaceutically acceptable salt or solvate thereof, wherein:

Y is in the 5-, 6-, 7-, and/or 8-position of the quinolone ring and Y is selected from:
(1) halo;
(2) —$NO_2$;
(3) —CN;
(4) alkyl;
(5) alkyl substituted with one or more halo atoms independently selected from F, Cl, Br, or I;
(6) alkenyl;
(7) alkynyl;
(8) cycloalkyl;
(9) cycloalkenyl;
(10) acyl;
(11) carboxyl;
(12) heterocyclyl;
(13) aryl;
(14) aralkyl;
(15) alkaryl;
(16) heteroaryl;
(17) aroyl;
(18) heteroaroyl;
(19) —$QR^3$, wherein $R^3$ is selected from alkyl, acyl, aryl, heteroaryl, aroyl, and heteroaroyl as defined above, and wherein Q is selected from S, O, and —$NR^4$ wherein $R^4$ is selected from:
(a) H;
(b) alkyl;
(c) acyl;
(d) cycloalkyl;
(e) heterocyclyl;
(f) aryl;
(g) alkaryl;
(h) aralkyl;
(i) aroyl
(j) heteroaryl; and
(k) heteroaroyl;
(20) —$OR^5$, wherein $R^5$ is selected from H, cycloalkyl, heterocyclyl, alkaryl, and aralkyl;
(21) —$CO_2R^{4'}$ wherein $R^{4'}$ is selected from H, alkyl, cycloalkyl, heterocyclyl, aryl, alkaryl, aralkyl and heteroaryl;
(22) —$N(R^4)_2$ wherein each $R^4$ is the same or different and when one $R^4$ is hydrogen and the other $R^4$ is acyl, the acyl group is alkenyl-C(O)-, alkynyl-C(O)- or cyclylalkenyl-C(O)-;
(23) —$S(O)_q R^{4'}$ wherein q is an integer from 1 to 2; wherein $R^{4'}$ is as defined hereinabove;
(24) —$SR^4$;
(25) —$Q_rC(O)R^6Z(R^{4'})_t$ wherein r is an integer from 0 to 1, Z is selected from N, S, and O, $R^6$ is an alkylene group having from 1 to 6 carbon atoms, t is 1 when Z is S or O, and when Z is N, then t is 2 and each $R^{4'}$ is the same or different;
(26) —$NHC(O)R^4$;
(27) —$NHSO_2R^{4'}$; and
(28) —$SO_2N(R^7)_2$, wherein each $R^7$ is the same or different and is independently selected from H, alkyl, and aryl;

n is an integer from 0 to 2 and when n is 2, each Y is the same or different;

X is heteroaryl wherein the heteroatom or heteroatoms in said heteroaryl must be nitrogen and wherein said heteroaryl is bound through a nitrogen atom;

m is an integer from 1 to 2;

W is aryl which is bound directly to the nitrogen atom and can optionally be substituted with up to three groups wherein each group is the same or different and is selected from:
(1) —OH;
(2) hydroxymethyl;
(3) alkyl;
(4) halo;
(5) —$NO_2$;
(6) alkoxy;
(7) —$CF_3$;
(8) —CN;
(9) cycloalkyl;

(10) alkynyloxy;
(11) alkenyloxy;
(12) —S(O)$_q$R$^{4'}$;
(13) —SR$^4$;
(14) —C(O)R$^8$, wherein R$^8$ is selected from —OH, —N(R$^4$)$_2$, and —OR$^9$ and R$^9$ is alkyl;
(15) —O—(CH$_2$)$_v$—C(O)R$^8$ wherein v is an integer from 1 to 4;
(16) —N(R$^4$)$_2$; and
(17) —NHC(O)H;
wherein q, R$^{4'}$ and R$^4$ are as defined above for Y;
with the proviso that in Formula (1) when R$^3$ and R$^4$ are heteroatom containing groups said heteroatom containing groups, when bound to a S, N, or O atom, is bound through a carbon atom of the heteroatom containing group.

2. A compound of claim 1 wherein Y is selected from:
(1) halo, wherein said halo is selected from F, Br, and Cl;
(2) —C(H)$_{3-b}$G$_b$ wherein b is an integer from 1 to 3 and G is a halo atom selected from F, Br and Cl;
(3) —OR$^{10}$ wherein R$^{10}$ is selected from H, alkyl, aryl, and heteroaryl;
(4) —O—C(O)R$^4$;
(5) —NO$_2$;
(6) —NH$_2$;
(7) —NHR$^{11}$ wherein R$^{11}$ is selected from alkyl, aryl, and heteroaryl;
(8) —NHC(O)R$^4$;
(9) —NHSO$_2$R$^{4'}$;
(10) —NR$^{12}$R$^{13}$ wherein R$^{12}$ is selected from alkyl and aryl, and R$^{13}$ is —C(O)R$^4$;
(11) —S(O)$_q$R$^{12}$ wherein R$^{12}$ is as defined in (10);
(12) —SH; and
(13) —SO$_2$N(R$^{10}$)$_2$ wherein each R$^{10}$ is the same or different and R$^{10}$ is as defined in (3);
wherein R$^4$, R$^{4'}$, and q are as defined in claim 1.

3. A compound of claim 1 W is selected from phenyl and substituted phenyl.

4. A compound of claim 1 wherein X is selected from: imidazolyl; pyrazolyl; pyrrolyl; and tetrazolyl.

5. A compound of claim 4 wherein W is selected from: phenyl and substituted phenyl.

6. A compound of claim 5 wherein n is 0.

7. A compound of claim 1 wherein X is selected from:
(a)

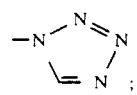

(b)

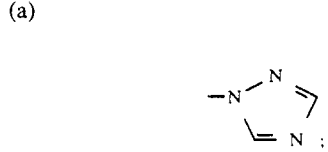

and
(c)

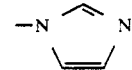

8. A compound of claim 6 wherein: m is 1, and W is selected from: phenyl and substituted phenyl.

9. A compound of claim 1 which is represented by formula (2)

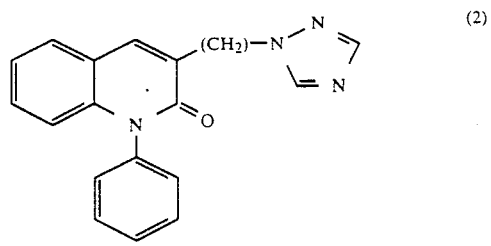

10. The compound of claim 1 which is represented by formula (3)

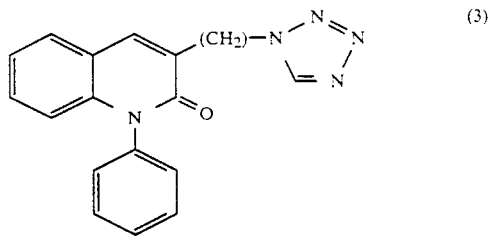

11. A compound of claim 1 represented by formula (1) wherein
m is one; and
W is substituted phenyl wherein said substituents are from one to three of the same of different groups selected from those defined in claim 1 for W; wherein q, R$^{4'}$ and R$^4$ are as defined for Y.

12. A pharmaceutical composition which comprises a compound of Formula (1) as defined in claim 1 in combination with a pharmaceutically acceptable carrier.

13. A method of treating allergy in a mammal comprising administering to said mammal an anti-allergy effective amount of a compound of Formula (1) as defined in claim 1.

14. A method of treating inflammation in a mammal comprising administering to said mammal an anti-inflammation effective amount of a compound of Formula (1) as defined in claim 1.

15. A pharmaceutical composition which comprises the compound as defined in claim 9 in combination with a pharmaceutically acceptable carrier.

16. A method of treating allergy in a mammal comprising administering to said mammal an anti-allergy effective amount of the compound as defined in claim 9.

17. A method of treating inflammation in a mammal comprising administering to said mammal the compound of Formula 2 as defined in claim 9.

* * * * *